(12) United States Patent
Allan

(10) Patent No.: US 8,602,837 B1
(45) Date of Patent: Dec. 10, 2013

(54) METHOD AND APPARATUS FOR IMPROVING THE UTILIZATION OF SOLITARY BEES FOR POLLINATION OF CROPS

(75) Inventor: Matthew James Allan, Easteigh (GB)

(73) Assignee: Pacific Pollination, LLC, El Dorado, AR (US)

( * ) Notice: Subject to any disclaimer, the term of this patent is extended or adjusted under 35 U.S.C. 154(b) by 448 days.

(21) Appl. No.: 13/047,522

(22) Filed: Mar. 14, 2011

Related U.S. Application Data

(60) Provisional application No. 61/313,992, filed on Mar. 15, 2010.

(51) Int. Cl.
*A01K 47/00* (2006.01)
(52) U.S. Cl.
USPC ........... 449/1; 449/4; 449/27
(58) Field of Classification Search
USPC ............ 449/1, 2, 3, 4, 12, 13, 26, 27
See application file for complete search history.

(56) References Cited

U.S. PATENT DOCUMENTS

| | | | |
|---|---|---|---|
| 3,994,034 A | | 11/1976 | Van Damme et al. |
| 5,895,310 A | * | 4/1999 | Otomo et al. ............ 449/1 |
| 6,364,738 B1 | | 4/2002 | Kendell et al. |
| 7,086,924 B2 | | 8/2006 | Mills |
| 7,556,552 B1 | | 7/2009 | Kemp et al. |
| 2007/0218804 A1 | | 9/2007 | Allan et al. |

* cited by examiner

*Primary Examiner* — Rob Swiatek
(74) *Attorney, Agent, or Firm* — James M. Duncan, Esq.; Klein DeNatale Goldner

(57) ABSTRACT

A processing unit for solitary bees is utilized in a method of timely providing a sufficient number of bees for pollinating a flowering crop. The processing unit provides secure storage for the solitary bees at every stage of their life cycle, and provides precise control of environmental conditions to ensure that the bees complete each stage of their life cycle in the optimum state of health and viability, and to ensure that adult bees emerge in close agreement with predicted emergence. The processing unit provides for protection against parasites, predators and pathogens, and may provide for feeding and mating of the bees. The processing unit may be used with any type of solitary bee nest. The processing unit may be fabricated in modularized components, allowing for increased capacity as required.

20 Claims, 31 Drawing Sheets

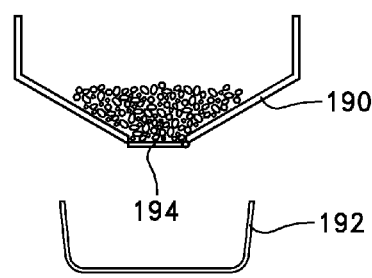 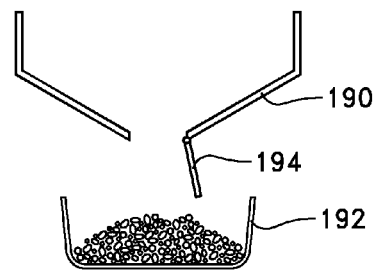
FIG. 17A          FIG. 17B
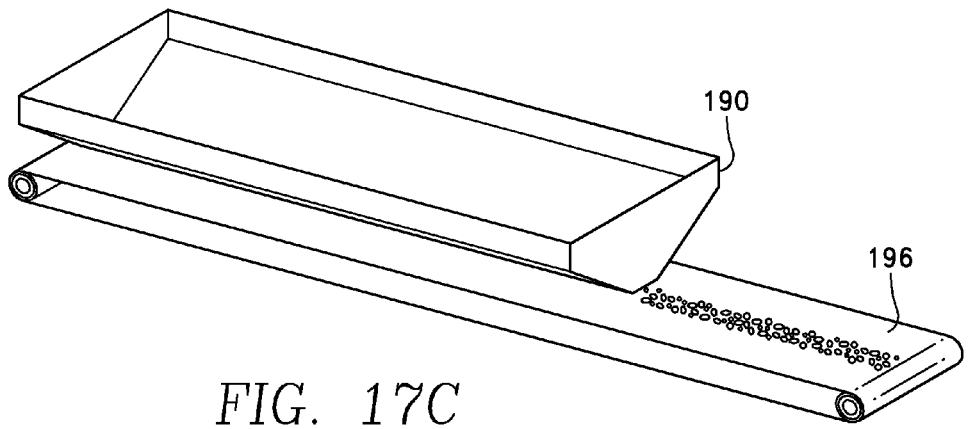
FIG. 17C

US 8,602,837 B1

METHOD AND APPARATUS FOR IMPROVING THE UTILIZATION OF SOLITARY BEES FOR POLLINATION OF CROPS

CROSS-REFERENCE TO RELATED APPLICATIONS

U.S. Application No. 61/313,992 for this invention was filed on Mar. 15, 2010, for which application this inventor claims domestic priority, and which is incorporated in its entirety.

BACKGROUND OF THE INVENTION

The present invention generally relates to the pollination of crops by bees, and more specifically to a unit for the storage and emergence of solitary bees and a method of utilizing the same.

Many crops benefit from pollination by bees, and some are highly dependent on bee pollination. These include the following food crops—almond, apple, avocado, blueberry, canola, cantaloupe, cherry, blueberry, cranberry, cucumber, kiwifruit, nectarine, peach, pear, pepper, plum, prune, raspberry, squash (including pumpkin and gourd), strawberry, sunflower, and tomato; and also crops for seed production, such as alfalfa, asparagus, beet, cabbage and other crucifers, carrot, clover and onion. Crops grown indoors such as in tunnels and glasshouses, and crops grown in very large areas frequently suffer from lack of natural pollinators.

Most commercial pollination is carried out using honeybees. The present invention is directed at an apparatus and method for improving the utilization of solitary bees as managed pollinators.

Solitary bees have a wide range of nesting habits. Some create cavities in which to nest, by mining or constructing cells; others (among them many species of Megachilid bee, such as *Osmia* and *Megachile* species) search for existing cavities, such as hollow plant stems, beetle borings in timber, pre-used nests created by other insects, and naturally occurring crevices. A female bee collects pollen which she packs into the cavity, then lays an egg on the pollen. The cavity is sealed containing one or several eggs which hatch into larvae and eat the stored pollen. Development is completed within the cavity. Eventually, adult bees emerge from the cavity to mate and continue the cycle.

Several species of solitary bee can be encouraged to use artificial nests. Such artificial nests can be used as trap nests to study existing populations; to improve habitats in order to attract bees or to boost populations; and to manage bees as pollinators in order to produce food crops and seed crops, and enhance pollination of wild flowers.

A number of strategies for artificial nests for solitary bees have been produced that seek to mimic the above-mentioned natural cavities. Nests may be formed from tubes. Hollow plant stems in which bees would naturally nest, such as reeds or bamboo, can be bundled together. These unsophisticated forms of nests are widely known and described, for example in Bosch J and Kemp W, 2001, "How To Manage the Blue Orchard Bee As An Orchard Pollinator", Sustainable Agriculture Network, p 20. Instead of using natural cavities provided by hollow plant stems, artificial tubes have also been widely used. These tubes include craft straws or drinking straws, as described in McGregor S E 1976, "Insect Pollination of Cultivated Crop Plants", United States Department of Agriculture, p 37. Thin-walled tubes and stems are vulnerable to parasitoid attack, so the use of thick-walled cardboard tubes has increased. Various cardboard tubes have been used, some incorporating a paper liner to improve removal and examination of the developing bees and also to deter parasitoid attack.

Nests may also be formed from grooved boards. Nests consisting of stacks of grooved boards are well known. The grooved boards are formed in such a manner that when stacked, they create an array of cavities therein. The grooves may be formed in a U-shape, which coincides with a flat face of an adjacent board to form a cavity, as described in Bosch J and Kemp W, 2001, "How To Manage the Blue Orchard Bee As An Orchard Pollinator", Sustainable Agriculture Network.

Alternatively, semi-circular grooves may be formed on both sides of each board of the stack, the semi-circular grooves of adjacent boards being aligned to create an array of cavities having a circular cross-section, as described in U.S. Pat. No. 5,372,535 and U.S. Pat. No. 5,618,220.

The flowering of most of the crop plants referred to above takes place over a limited period. In order to achieve effective pollination on a commercial scale it is necessary to ensure that bees are on site and available to forage on the flowers during that period. When honeybees are used, this is a matter of bringing hives with large populations of workers to the site in time. Solitary bees have a different life cycle which requires an entirely different management strategy.

In the spring and early summer, solitary bees in the wild are stimulated to start the process of emergence by longer periods of higher temperature. It may be that a small grower of say apples will be fortunate in that a wild population of solitary bees emerges reliably around the time that the trees flower. However commercial pollinators must be in a position to influence the time of emergence to delay or bring forward the activity of the bees to match the flowering of the target crop.

In the wild, solitary bees overwinter either as dormant adults or as prepupae. The emergence of certain species of solitary bee, for example *Osmia rufa, O. cornuta* and *O lignaria*, may take place over an extended period, in cases up to a month. In addition the males start to emerge first, with the females following a few days or a week later. Although the general pattern of emergence is well known, it can be difficult to predict with accuracy what percentages of males and females will have emerged by a certain date under a certain temperature regime. The use of degree-day models is well known in agriculture and science to predict various biological phenomena such as the commencement of growth of specific plants, the opening of flowers or buds, or the activity of insects, but the application of degree-day modeling to management of solitary bees is not precise enough at the present time.

One known approach to providing flying solitary bees on crops to be pollinated is to warm the cocoons until sufficient active adults have emerged. These bees are chilled again, then transported to the pollination site and released. This procedure means that the earliest of the emerging females are held for a number of days after emergence, before deployment in the field, a factor which may contribute to the high dispersal rate that is sometimes observed when active adult bees are released direct into the orchard. This may require many more bees to be released than are actually necessary to carry out the pollination. Another approach is to warm the cocoons (either by staged temperature increases or directly from chilled temperature to incubation temperature) to a point at which it is calculated the bees are close to emergence, then transport the cocoons to the pollination site and allow the bees to emerge under ambient conditions. A drawback of this procedure is that if temperatures drop the emergence may be delayed for a considerable period, so that the number of flying bees is reduced or even zero at the critical period for pollination.

After the flowers have fallen from the crop, and no females are still active, the nests are removed from the orchard, field, glasshouse, etc and transported to a central facility for further handling. In the known practice, this may include emptying of nests; washing or cleaning the cocoons; sorting the cocoons by sex; examining for parasites and disease; carrying out hygienic measures; storing the cocoons in appropriate conditions; examining bees to determine stage of development; placing in cold store for winter; removing from the cold store; and deploying emerging adults into orchards, fields, etc.

SUMMARY OF THE INVENTION

Embodiments of the disclosed apparatus and method provide improvements to the procedure described above. These improvements over the known apparatus and methods include one or more of the following:
- provide secure storage for solitary bees at every stage of their life cycle apart from when they are active adults released on crops for pollination and/or replication;
- provide precise control of environmental conditions to ensure that bees complete each stage of their life cycle at the optimum time, in the optimum state of heath and viability;
- provide precise control of environmental conditions to ensure that adult bees emerge in close agreement with predicted emergence;
- provide the means to easily and accurately adjust rate of emergence to (a) match predicted emergence, and (b) respond to faster or slower flower development on the crop;
- provide protection against parasites, predators and pathogens by (a) preventing access to stored bees and nests, and (b) providing means to eliminate, reduce or remove parasites, predators and pathogens that are present in the stored bees and nests;
- provide means for newly emerged adult bees to feed, so that bees arrive in crops well-fed;
- provide means for bees to mate prior to deployment in crops
- may be loaded once only each year with nests, nest components or loose cocoons and unloaded the following year after the bees have emerged and been deployed on crops;
- may be used with any type of solitary bee nest;
- provide means and a method for accurately predicting the emergence of any population of bees;
- provide different populations with different environmental conditions;
- provide active adult bees for deployment on crops in a planned constant stream so that bees may be deployed soon after emergence without being held for excessive periods either at high incubation temperatures or at low chilling temperatures, the stream of emerging bees being planned to match the predicted demand for bees;
- provide the means for the emerged adult bees to separate themselves from nests and cocoons with minimum operator intervention;
- provide flexible and optionally modular systems so that operators may easily expand their facilities in line with population increases;
- provide solitary bees for pollination services with minimal labor input.

In summary, the presently disclosed apparatus and method may provide: (a) the optimum conditions for large numbers of solitary bees such as *Osmia lignaria* throughout their development and over winter, (b) accurately control the emergence of the bees to match the flowering of the target crop to be pollinated, (c) facilitate the removal of emerged bees for subsequent deployment with minimum operator involvement. The disclosed apparatus can be used with any of the above described nests, or with loose cocoons, or with any combination of these. The disclosed apparatus eliminates the need for large numbers of expensive field incubators. The disclosed method provides for the efficient utilization of bees for pollination of crops.

BRIEF DESCRIPTION OF THE DRAWINGS

FIGS. 17a-17c show alternative collection means for bees.

DETAILED DESCRIPTION OF THE EMBODIMENTS

Figure 1:
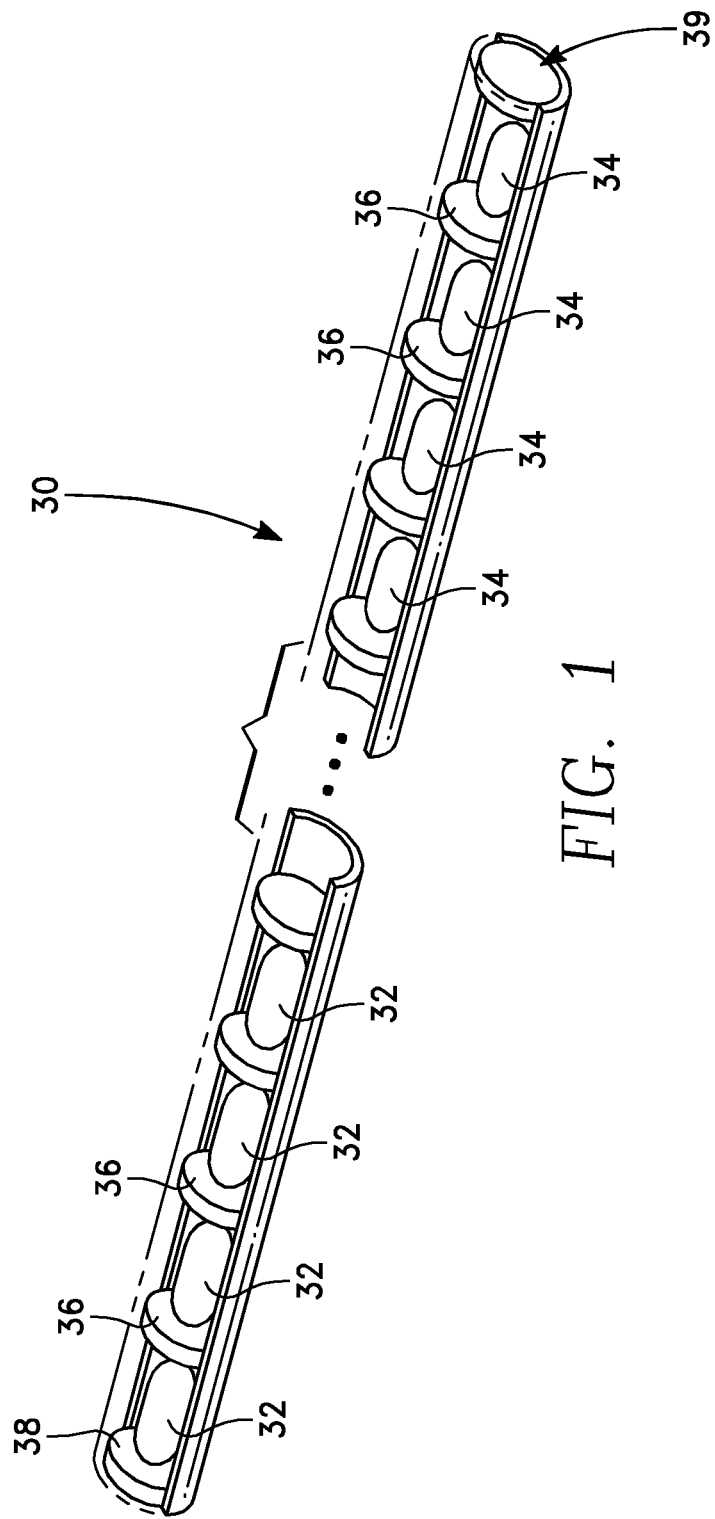
FIG. 1 shows a section of a typical nest.

FIG. 1 shows a section of a typical nest 30, which may be natural (e.g., a reed) or artificial (e.g., a cardboard tube) containing both female 32 and male 34 cocoons. It should be noted that the sequence of sexes of the bees as shown is typical, i.e., the first eggs laid (at the base 38 of the nest) are females, and the ones nearer the entrance 39 are male. Each cell is formed by a seal 36 which the mother bee constructs, typically of mud, but different species use different materials.

Nests may alternatively be formed in solid blocks of material, for example, by drilling as described in Cane J, Veirs D and Trostle G, 2003, "How To Build A Nesting Block" USDA-ARS-NPA, Bee Biology And Systematics Laboratory, Logan, Utah, www.loganbeelab.usu.edu. Wood is commonly used as the block material. However, blocks complete with cavities may also be moulded from plastic. Similar to tube nests, additional liners have previously been provided to improve removal and examination of the developing bee.

The invention disclosed herein comprises embodiments of a unit 40 for the storage and emergence of solitary bees. One embodiment is shown in perspective in FIG. 2 and in cross-section in FIG. 3. In its simplest form the apparatus (or "Unit") provides a process chamber 42 in which immature bees within nests or loose cocoons are placed. The process chamber is connected to an attached flight chamber 44 into which emerged bees pass after they become active, and in which, if desired, the emerged bees may be chilled in order to render them immobile for collection. Another embodiment may comprise two or more process chambers which are linked to a flight passage along which the bees fly to a chilling chamber.

The unit 40 may provide conditions appropriate for the bees (after they have been removed from the orchard, field, glasshouse, etc) during the following sequential stages of their lives:
  hatching of the egg on the pollen provision and the emergence of the larva
  development of the larva through its instars while it feeds on the stored pollen
  development of larva to prepupa and the spinning of the cocoon
  pupation, during which the bee changes from a pupa into an adult
  overwintering of the adult bee inside the cocoon
  emergence of each bee from its cocoon In each case above, the appropriate environmental conditions and stimuli are provided by embodiments of the apparatus to ensure the optimum conditions for the bee at each stage, while minimizing or eliminating handling. Unit 40 is flexible in use. For example the operator may choose to use the apparatus to provide conditions for bees in any, and not necessarily all, of the above stages.

In addition, embodiments of the apparatus 40 provide a method of separating and collecting emerged adults in the optimum condition for pollinating with very low labor inputs. As each bee emerges, it is attracted out of the warm dark incubation conditions of the process chamber 42 into the adjacent brightly illuminated flight chamber 44. If desired, flight chamber 44 may be periodically chilled, rendering the bees in it inactive. These are collected and held briefly, preferably in cold storage, before transport to the orchard, field, etc where they are released for pollination.

Embodiments of the apparatus are designed for commercial growers and pollinators, particularly those involved in the production of almonds, cherries, apples, pears, strawberries, plums. However, embodiments of the apparatus may also be used for many other crops, including those for seed production. Embodiments of the apparatus are particularly effective when used in large scale operations where millions of solitary bees are being handled.

One consequence of using solitary bees as pollinators is that the population of the bees tends to increase each year, typically by a factor of two to four. The operator must make allowance for regular increase in plant capacity, or otherwise dispose of excess population of bees each year by sale, lease, donation etc. (For the purposes of illustration, when any details of the unit are quantified in the following description, this will refer to a unit capable of handling one million bees, unless otherwise stated.) Embodiments of the disclosed apparatus are flexible in design, and may be installed as modular units, permitting the operation to expand incrementally.

At different stages of development of the bees, the optimum conditions vary. Embodiments of the disclosed apparatus are designed to provide the following illustrative conditions. Different species of bees working different crops in different ambient conditions will have different requirements. Embodiments of the disclosed apparatus are sufficiently adaptable to provide whatever conditions are necessary.

| Stage | Approximate duration (days) | Temp (deg C.) | Relative Humidity |
|---|---|---|---|
| Hatching egg | 6 | ambient | ambient |
| Larva | 14 | 28 | |
| Prepupa | 28 | 28/18 fluctuating | |
| Pupa | 25 | 28 | |
| Adult | 194 | 4 | 95 to 50 |
| Emerging adult | 15 | 28 | 30 |

Figure 2:
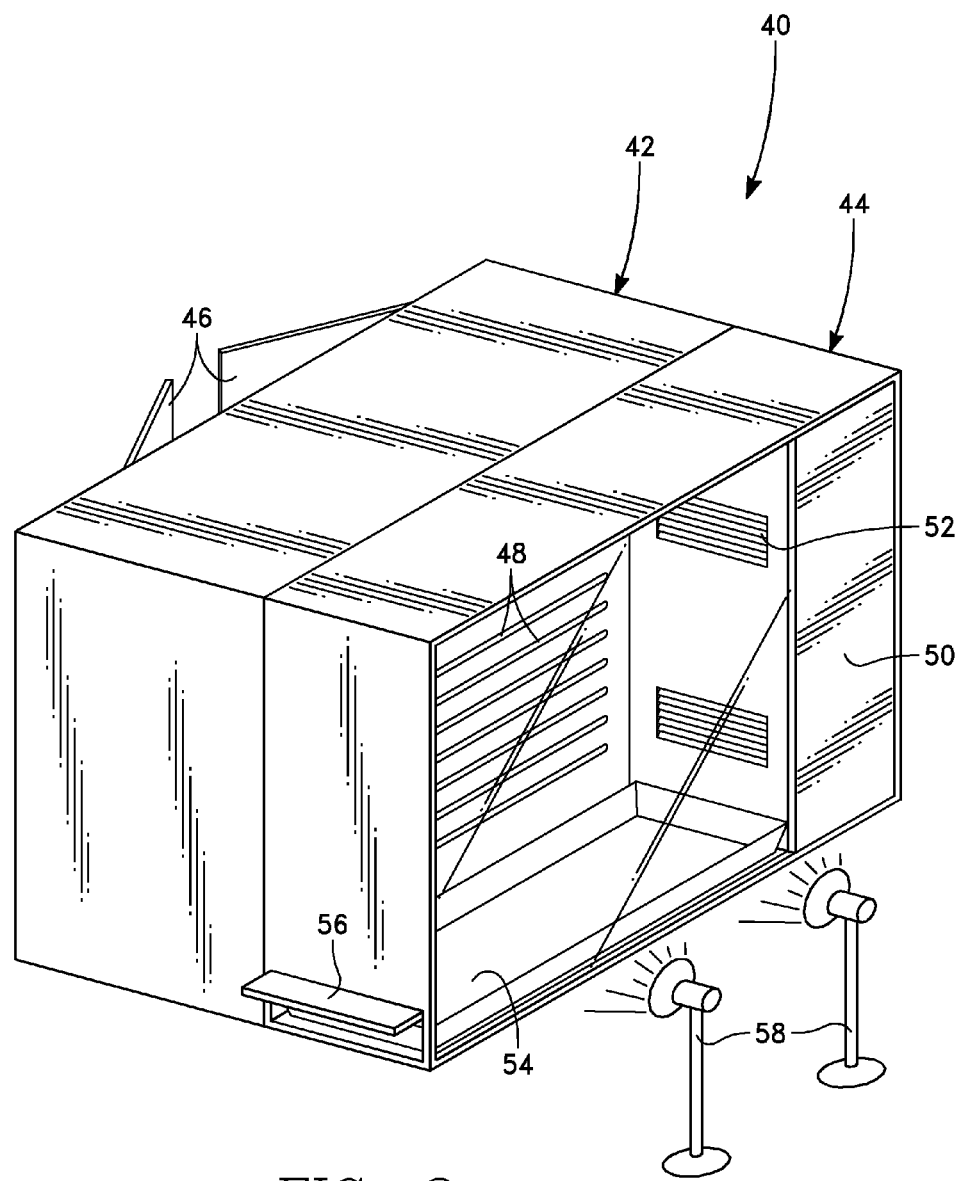
FIG. 2 shows an embodiment of an apparatus for storage and emergence of solitary bees.
Figure 3:
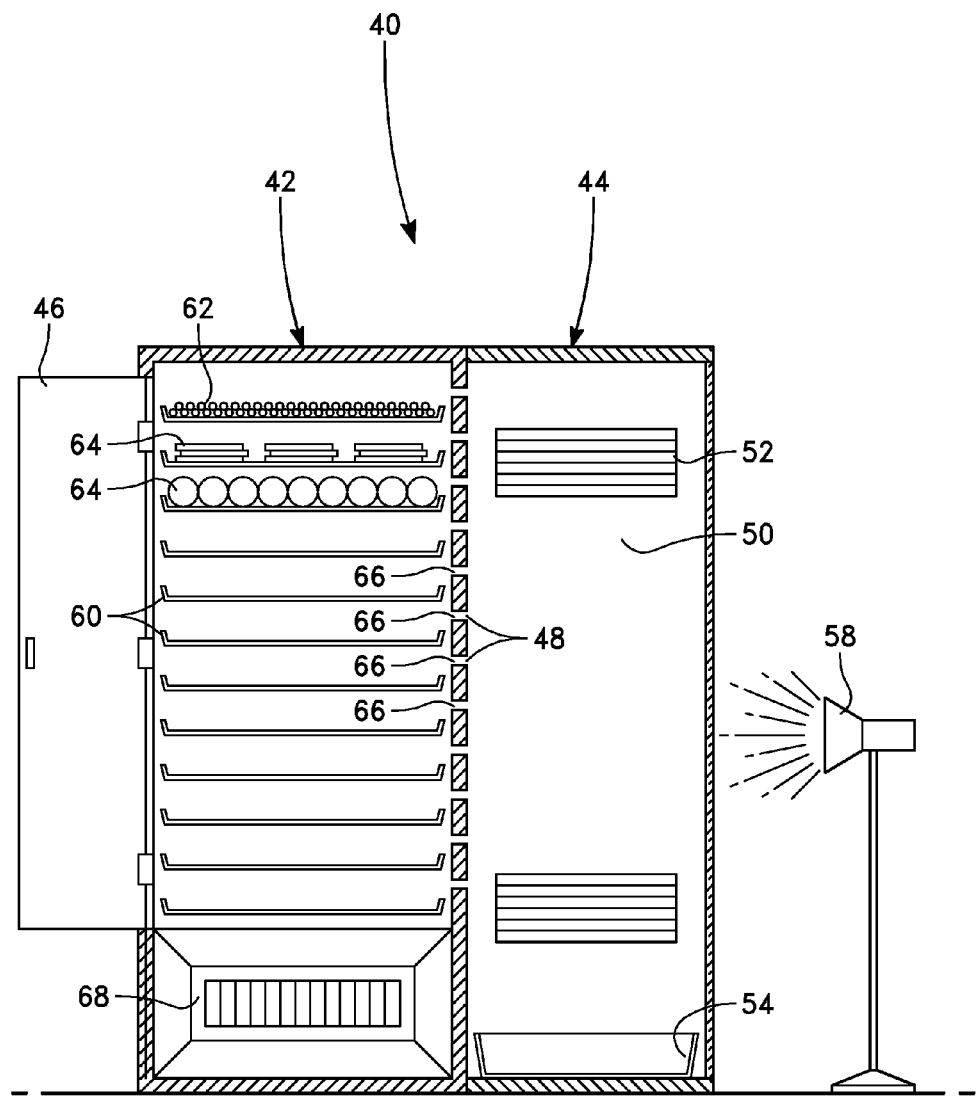
FIG. 3 shows a sectional view of an embodiment of an apparatus for storage and emergency of solitary bees.

Nests 30 are brought to a processing facility containing one or more of the disclosed units 40. The bees, which are at this stage may be undergoing several stages of development inside cocoons, are placed inside the apparatus in one of several ways: (1) enclosed within their nests; (2) within opened nests; (3) as loose cocoons in trays; or (4) in some other condition. An airflow is passed over the bees. The airflow is conditioned to provide cooling or heating to the bees, and it may be further controlled to provide required humidity levels. FIGS. 2 and 3 show perspective and sectional views respectively of embodiments of a process chamber 42 and an associated flight chamber 44. Bees are loaded into process chamber 42 on trays or other supports 60 through doors or other openings 46. They may be in the form of loose cocoons 62, or enclosed in parts of nests or whole nests 64. When the bees have been stimulated to emerge, they are attracted by illumination 58, and exit through passages 66 which lead to openings 48 into flight chamber 44. The heating, ventilating and airconditioning plant 68 in this embodiment is below process chamber 42.

Figure 4:
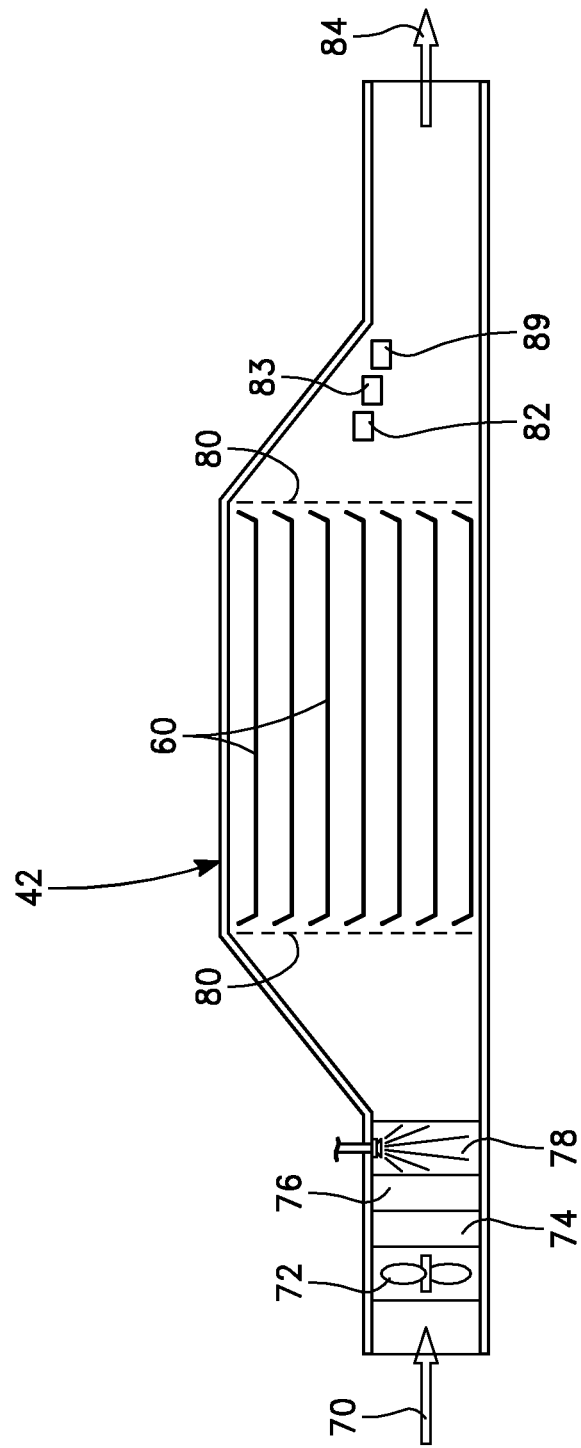
FIG. 4 schematically shows the airflow through an embodiment of an apparatus for storage and emergence of solitary bees.

FIG. 4 is a schematic, showing the input airflow 70 and the discharge airflow 84 for an embodiment of a process chamber 42. For the purposes of control, temperature sensor 82 and optional humidity sensor 83 and optional carbon dioxide sensor 89 are preferably located in the discharge airflow 84, because the bees within process chamber 42 are contributing metabolic heat and water vapor. Locating the sensors in the airflow at the entrance to the process chamber 42 may lead to inaccurate control.

Figure 5:
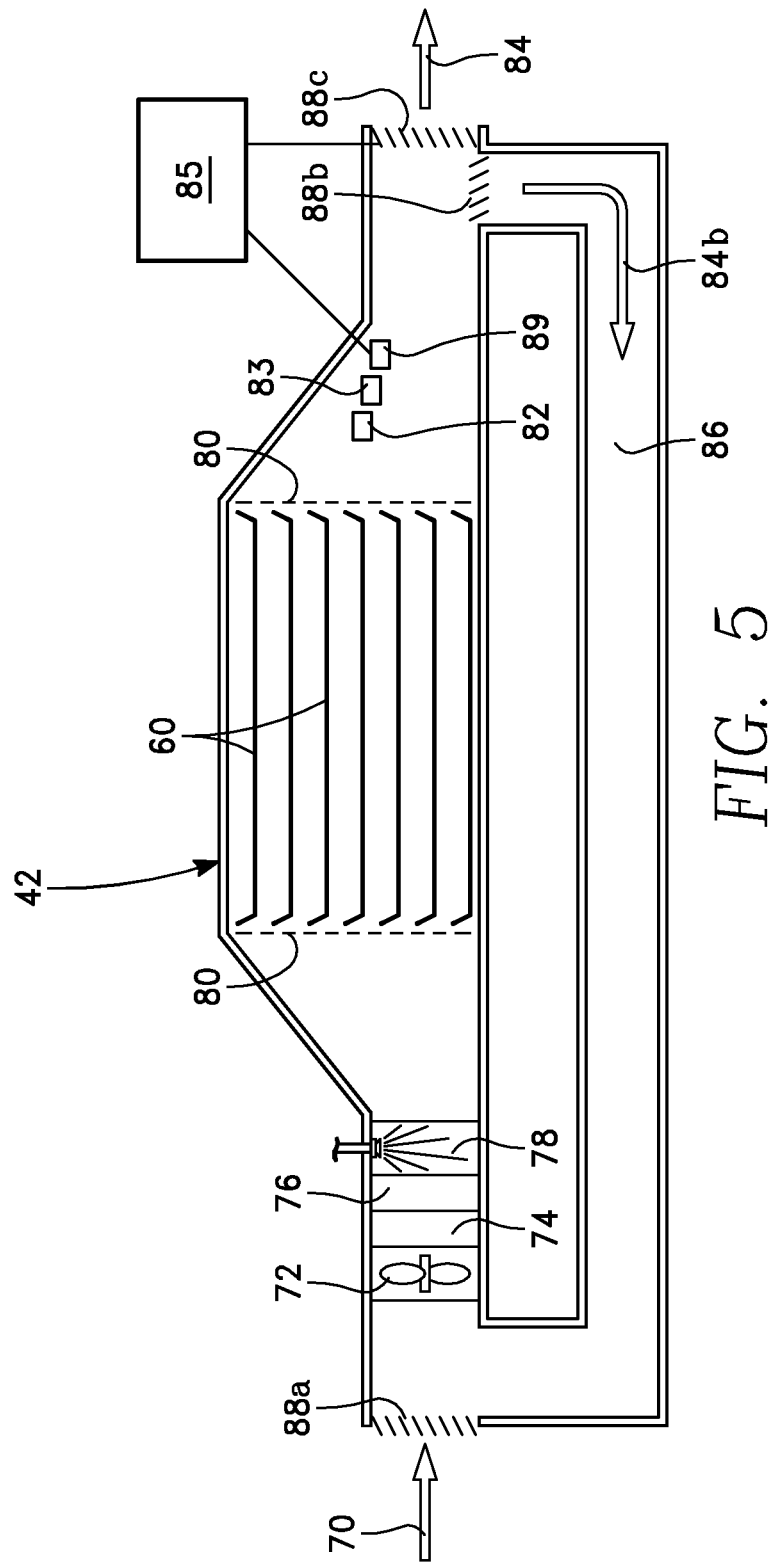
FIG. 5 schematically shows the airflow through an embodiment of an apparatus for storage and emergence of solitary bees, showing how the airflow may be recycled through a return duct.

For some embodiments, the output air is not discharged, but may be recycled through a return duct or passage 86, as shown in FIG. 5. (Note that the flight chamber is omitted for clarity). Recycling the conditioned air is more energy efficient. However, the bees inside the apparatus are living organisms, and hence consume oxygen and produce carbon dioxide and water vapor in the course of respiration. The system therefore cannot be hermetically sealed, but allowance must be made for a proportion of the air handled to be fresh air to maintain oxygen levels and reduce carbon dioxide levels. In practice, the natural leakage that occurs in such systems may be sufficient to provide sufficient fresh air for the bees to breathe. However it should not be assumed that this is the case, and where the scale of the Apparatus is substantial (i.e., handling perhaps a million bees or more), the design should incorporate means for mixing some fresh external air with the recycled air. This may be done by conventional arrangements of interlinked dampers 88a,88b,88c as shown in FIG. 5. These may be manually set, or automatically controlled where the ratio of fresh recycled air is controlled by adjusting interlinked dampers 88a, b and c in response to signals from carbon dioxide sensor 89.

It is a feature of the disclosed apparatus that each bee is not left exposed to incubation temperatures longer than necessary. Each bee emerges from its cocoon inside a dark warm chamber. In order to collect the bees for deployment for pollination, they have to be removed from the unit 40. Active bees exhibit positive phototaxis, i.e., they move towards light. As shown in FIG. 3, the process chamber 42 comprises passages 66 which may be brightly illuminated exits which the bees can walk or fly towards and through, reaching the flight chamber 44. Passage 66 may be fitted with non-return devices, such as flaps or angled hairs or fibres, or they may be geometrically designed so that bees find it difficult to return to the process chamber 42. The passages 66 may have closures so that when the bees are not active, i.e., during the whole of the development period and most of the winter, heat is not lost or gained by air movement through the passages.

Figure 6:
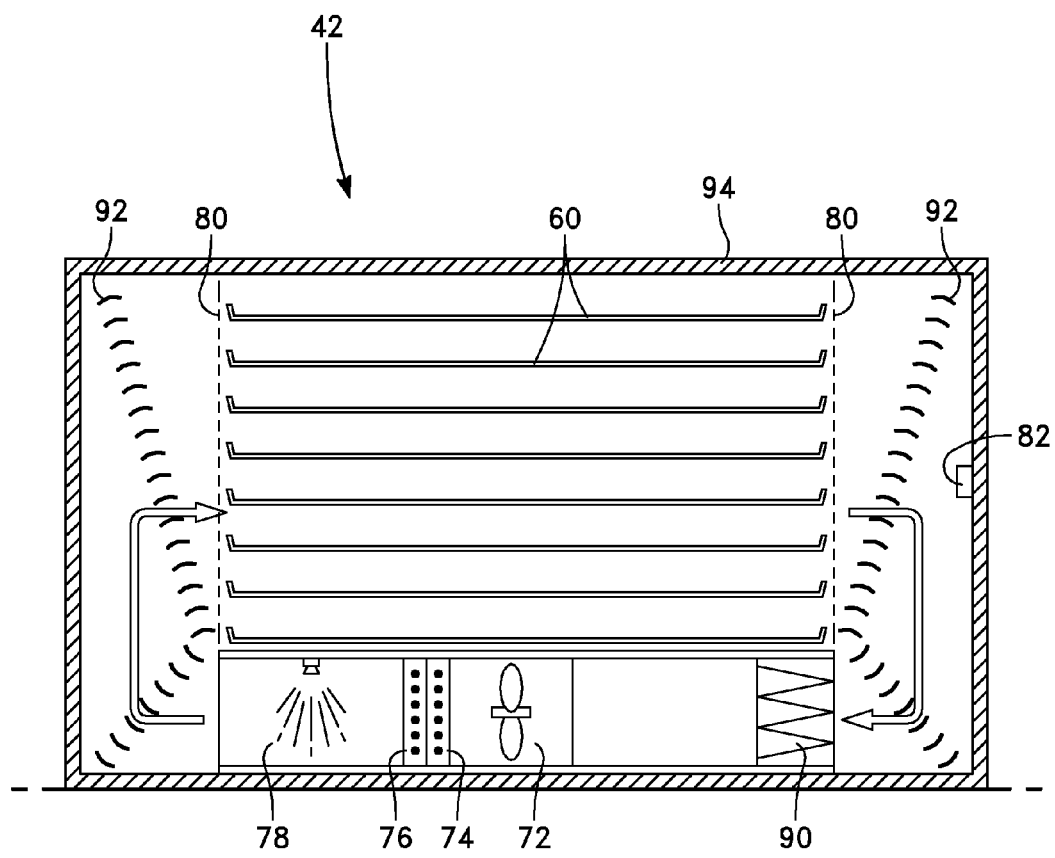
FIG. 6 shows a vertical cross-section of an embodiment of the disclosed apparatus, showing a possible configuration of the components of the apparatus.

One possible configuration of an embodiment of the apparatus is shown diagrammatically in FIG. 6 in vertical cross-section, showing the disposition of plant components in more detail. Conventional heating, ventilating and air conditioning components are shown as they might be fitted to an embodiment of the unit 40. The system may also comprise a source of hot water, a source of cooling fluid, and a source of humidifying water, each which may be located at a distance from the system. Flight chamber is omitted from FIG. 6 for clarity. In FIG. 6 the HVAC plant is located under process chamber 42. Access to the interior of process chamber 42 is through doors or other openings 46 at high level, which requires that the bees (either within nests or as trays of loose cocoons) are manually or otherwise lifted to that height.

As further indicated in FIG. 6, the flow of air through process chamber 42 may be guided by turning vanes 92 to maintain equal and even airflows over and under each tray 60. A feature of embodiments of the apparatus is to ensure that each bee experiences the same environmental conditions to ensure precise control of emergence. Bees located in areas of stagnant airflow will experience undesirable temperatures and humidities, which may affect the speed of development and the speed of emergence; this may reduce the viability or vigor of those bees and compromise the efficiency of the pollination operation.

There are many options for the physical layout of various embodiments of the apparatus and associated plants; the detail design will depend on many factors, such as the space available, operational decisions, permanence of the establishment, state of growth. Skilled operators in the field of heating, refrigeration and airconditioning who understand the principles of the apparatus will be capable of adapting the design to suit many circumstances.

Figure 7A:
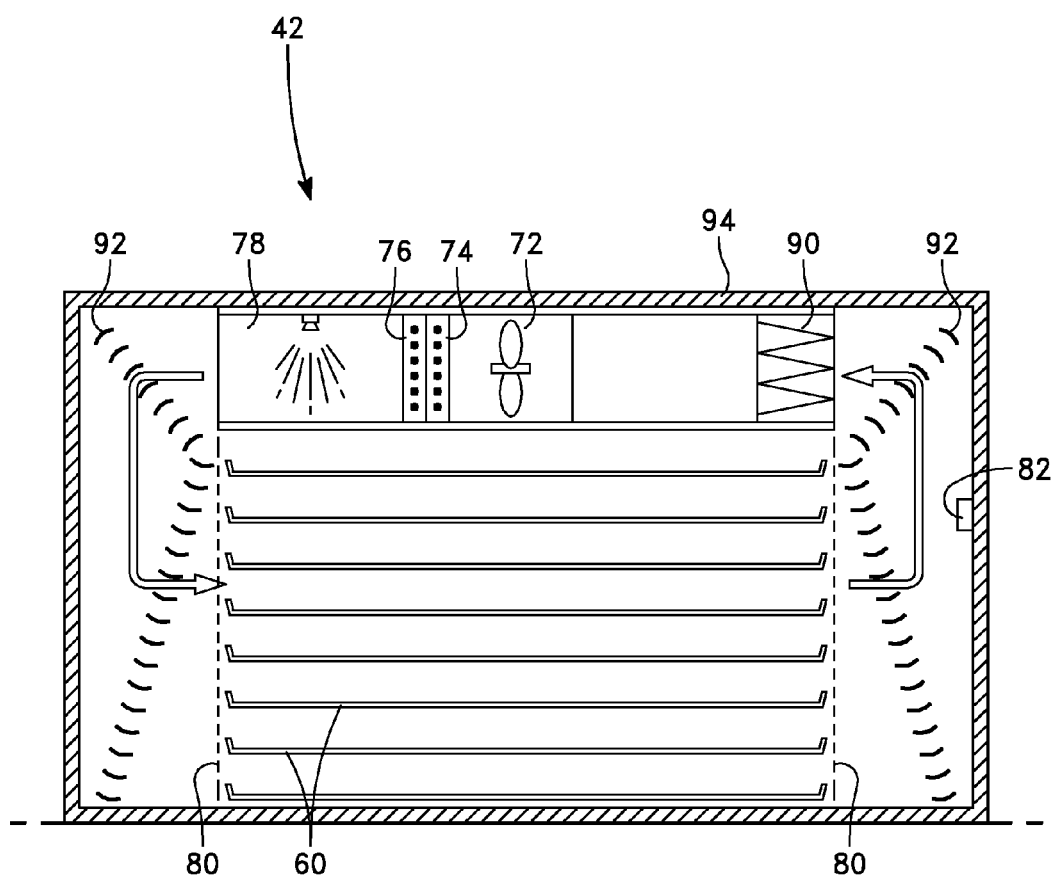
FIGS. 7a and 7b show vertical cross-sections of embodiments of the disclosed apparatus, showing other possible configurations of the components of the apparatus.
Figure 7B:
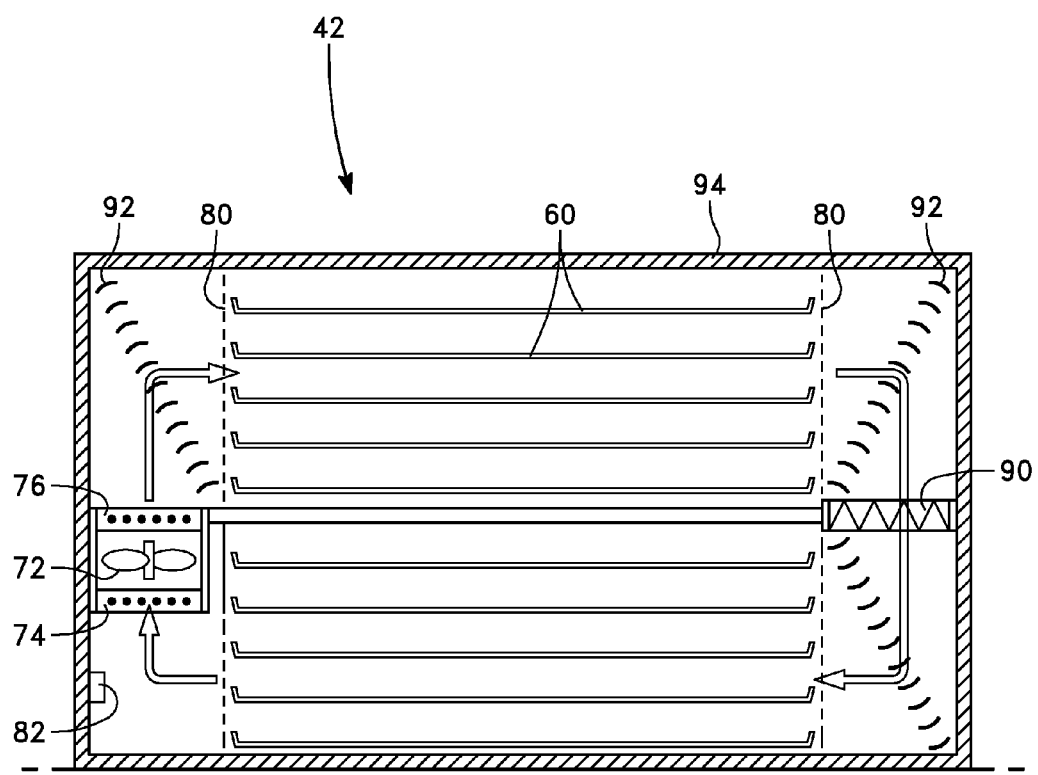

FIGS. 7a and 7b schematically show two further options in physical arrangement for embodiments of the apparatus. It is to be noted that the flight chamber is omitted from FIGS. 7a and 7b for clarity. While FIG. 6 shows an embodiment in which the HVAC plant is below process chamber 42, in FIG. 7a the HVAC plant is located above process chamber 42, which enables access to the interior of process chamber 42 to be by full-height doors 46. This permits the use of trolleys to transfer the bees and/or nests in and out of the Unit and simplifies handling. In the embodiment shown in FIG. 7b, the plant is located at one end of process chamber 42. This ensures easy access to the plant for maintenance. Access for moving nests and/or bees is once again by full-height doors 46.

In low light conditions, such as may be present in embodiments of the process chamber 42, bees have difficulty in flying. It is desirable therefore that the route from trays of cocoons 62 or nests 64 is continuous and unimpeded so that bees can walk directly towards the light at the exit passages. In order to facilitate the rapid escape of newly-emerged bees, passages 66 may be aligned so that they permit light to shine directly onto the top of the layer of cocoons 62, or the point at which bees exit nests 64 or nest components.

The choice of construction methods for embodiments of the apparatus will depend on many factors, such as cost, location, method of operation, growth potential, etc. There are many known and widely used construction methods which would be applicable. The following are illustrative examples of methods which may be utilized for construction of different embodiments of the disclosed apparatus.

Figure 8:
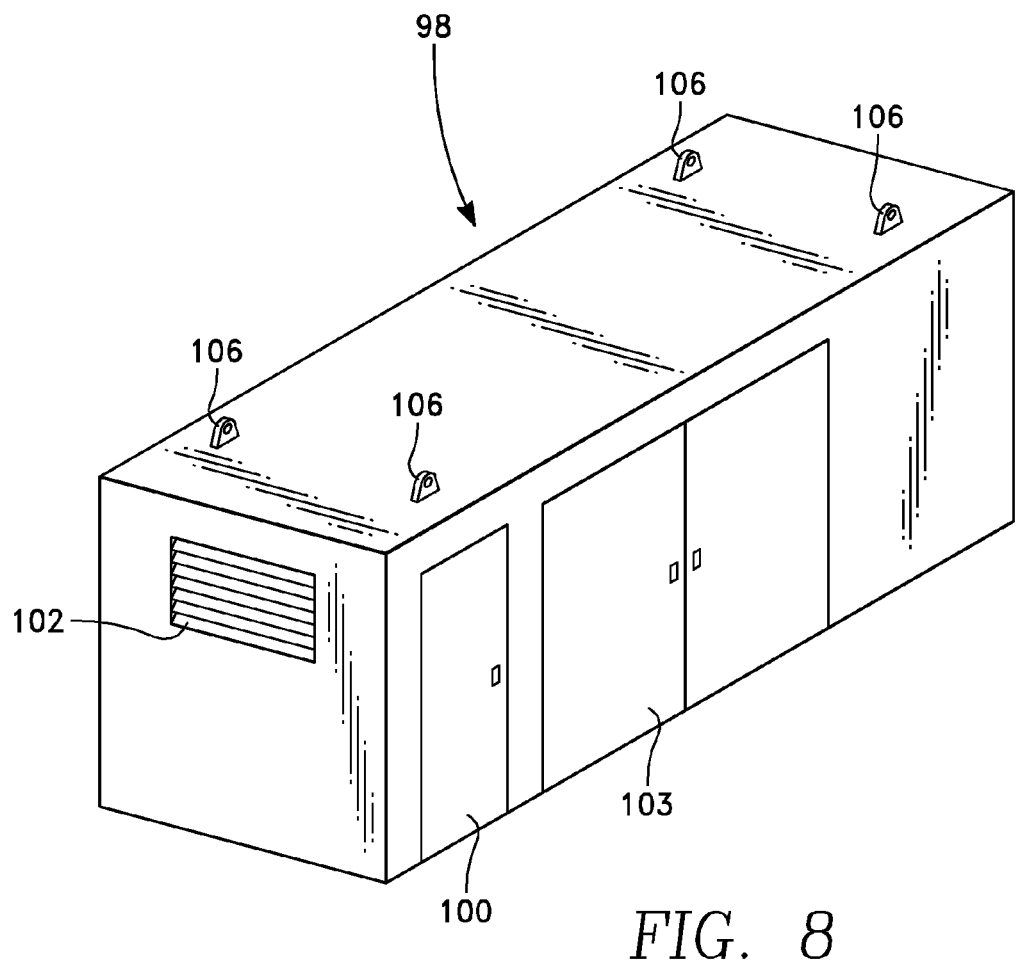
FIG. 8 shows an embodiment of a known industrial air handling unit which may be utilized in conjunction with embodiments of the apparatus.

FIG. 8 shows an industrial air handling unit 98 which may be utilized for providing heating, ventilation and air conditioning, where process chamber 42 may be an integral component of the unit. Alternatively, the air handling unit 98 may be connected to one or more process chambers 42 with a ducting system. Air handling unit 98 is generally a structure of welded steel section with a steel skin (although they may be constructed of other materials) forming a chamber which houses all the components specified by the engineer, which may include process chamber 42. These units are factory assembled and commissioned and delivered by truck complete to site once tested. On-site commissioning is quick and simple. Flight chamber 44 is omitted from FIG. 8 for clarity. Door 100 allows access to heating, ventilating and airconditioning plant. Doors 103 allow access for loading bees. Fresh air is drawn in through air inlet 102. Unloading and positioning is by use of lifting points 106.

Figure 9:
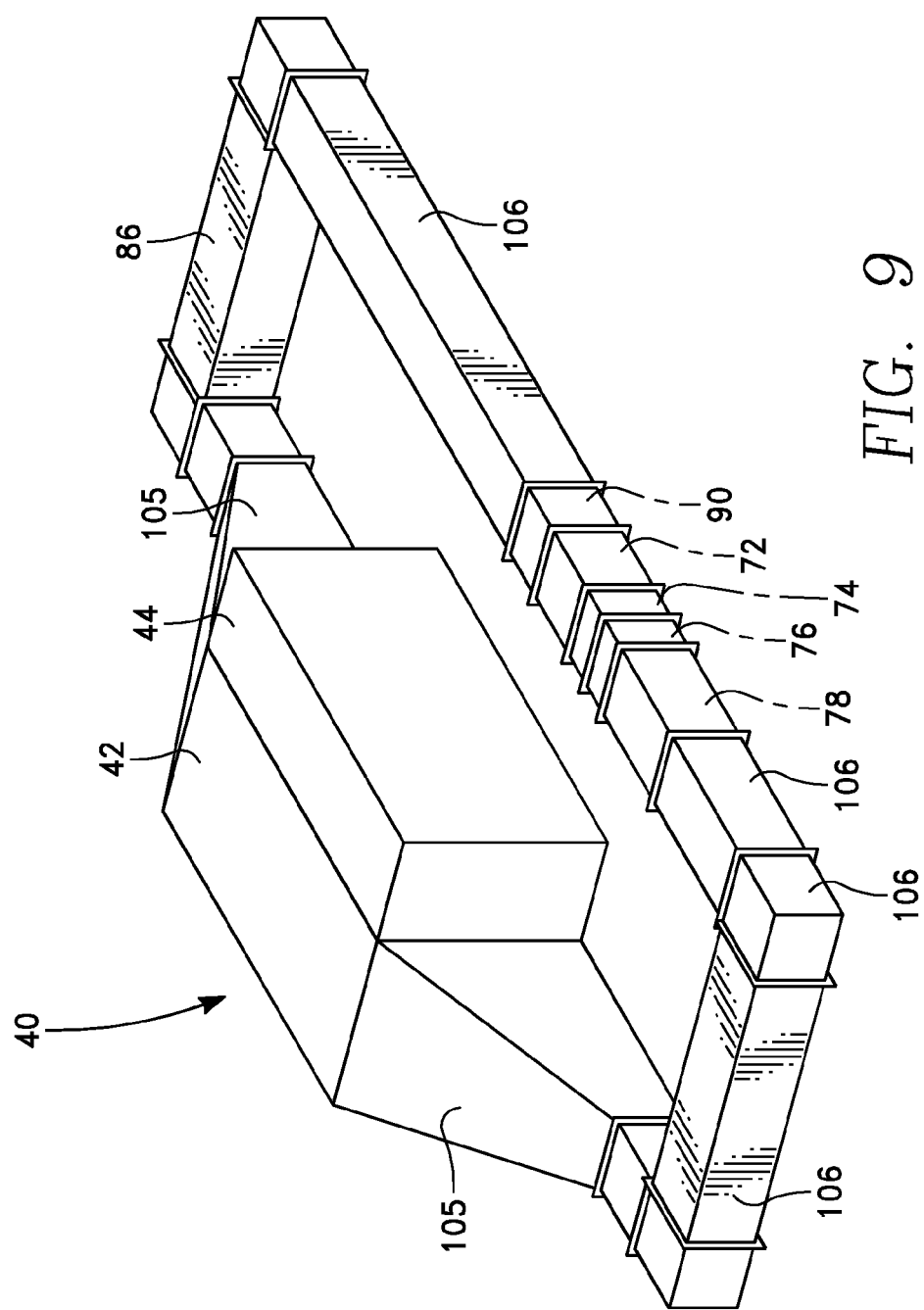
FIG. 9 shows an embodiment of the apparatus which has been configured in conjunction with conventional HVAC components.

As an alternative to the industrial air handling unit 98 shown in FIG. 8, FIG. 9 schematically shows an embodiment in which individual components are specified by the engineer and the assembly of the components takes place on site. FIG. 9 shows an embodiment assembled using conventional heating and air conditioning components, e.g., plenum 105, ducts 106, fan 72, cooling coil 74, heating coil 76, humidifier 78. Insulation may be applied by known commercial methods. The construction of the process chamber 42 may be whatever is considered appropriate; it may be regarded as an extension of the ductwork, or other engineering or architectural considerations may dictate the construction method.

Figure 10:
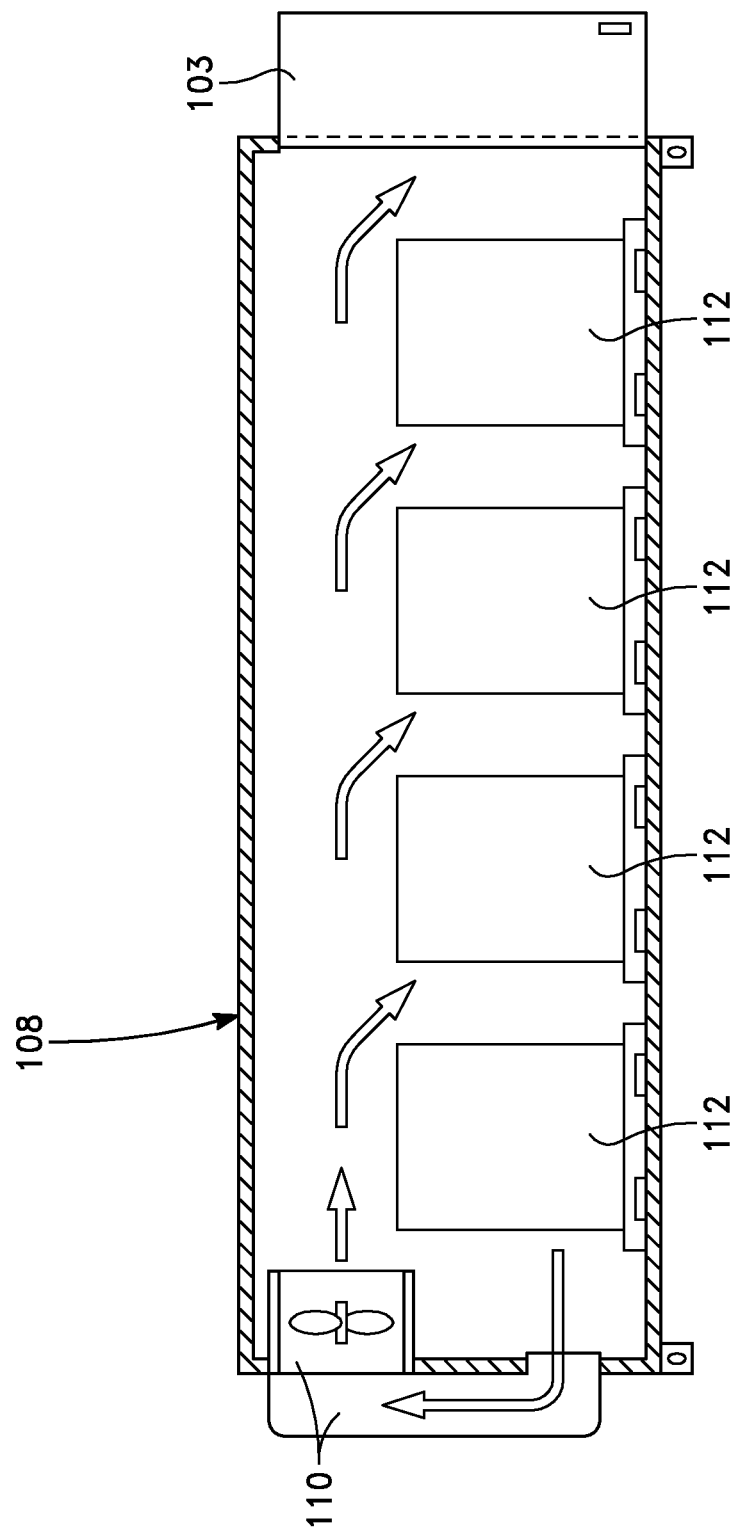
FIG. 10 schematically shows an embodiment of a refrigerated shipping container which may be utilized in conjunction with embodiments of the apparatus.

FIG. 10 shows another alternative configuration in which a refrigerated container utilized in the freight industry is adopted for use. An embodiment of the apparatus using such a container is schematically shown in cross-section in FIG. 10. In this embodiment, steel container 104 is built to the conventional dimensions, typically 20 ft or 40 ft long×8 ft wide×8 ft or 9 ft high, with refrigeration plant 110 mounted externally at one end. Manufacturers also build such units to specific requirements, for example the provision of heating in addition to refrigeration, and controlled fresh air inlets when the contents include living organisms. The structure is very strong, built to withstand years of exposure to sea conditions, repeated crane handling, and stacking several high. A number of manufacturers offer variations on the basic refrigerated container, including fresh air inlets for live goods and heating capability.

The airflow within the container is different from that described previously, in that fans move the air around vigorously within the container, but there is no specific ducted recirculation route. In this arrangement, the containers 112 containing bees should be arranged in a more open arrangement to ensure that air distribution is adequate, avoiding stagnant areas. Additionally it may be advisable to specify the fan duty in this circumstances such that the air is circulated at a higher speed. Except for flight chamber 44, which is omitted from FIG. 10 for clarity, these units are self-contained, requiring only an electric supply for operation. Sophisticated controls are available, as is a back-up power system, commonly a diesel generator which cuts in automatically in the case of electricity failure. Units based on shipping containers are relatively cheap, reliable, and can be relocated easily.

Figure 11:
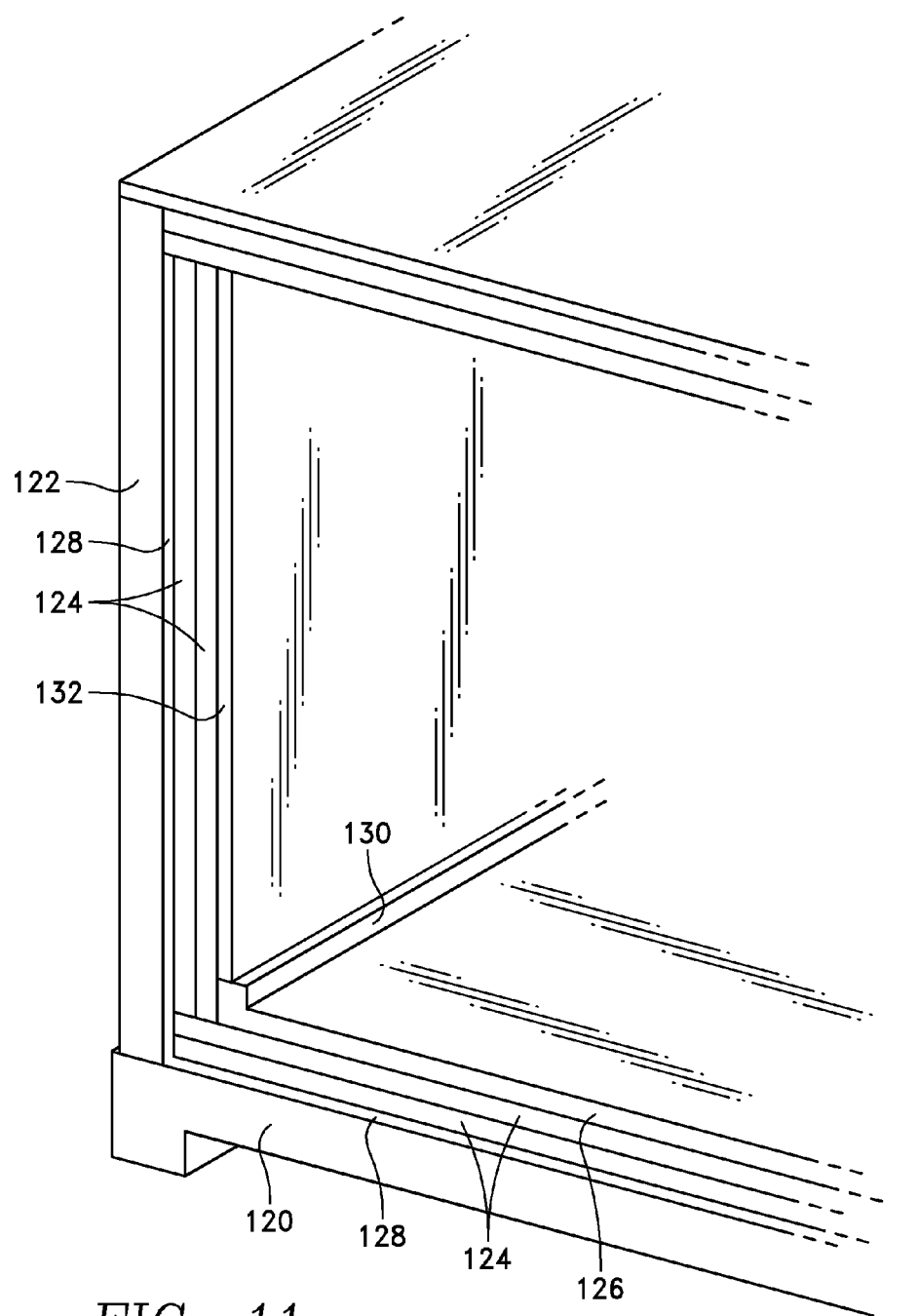
FIG. 11 shows a portion of a climate-controlled room which may be utilized in conjunction with embodiments of the apparatus.

As yet another alternative, in certain circumstances it may be preferable to construct embodiments of the process chamber in a conventional manner as part of a building, where the services are provided as with normal building services. Coldrooms and climate-controlled rooms are well known in architecture. Embodiments of the process chamber may be built on-site with conventional building materials including substantial insulation. Alternatively, embodiments of the process chamber may be provided by a specialist manufacturer as prefabricated components assembled on-site. FIG. 11 shows a detail of an embodiment of a building having a climate-controlled room which may be utilized for processing unit 40. Base slab 120 and structural wall 122 are lined with waterproof membrane 128. One or more layers of insulation 124 are fixed to walls, floor and ceiling. Floor surface 126 is laid with upstand 130. The walls and ceiling are finished with washable surfaces 132.

In all cases, thermal insulation should be installed as appropriate to increase efficiency and to maintain stable environmental conditions inside the process chamber and flight chamber.

Figure 21:
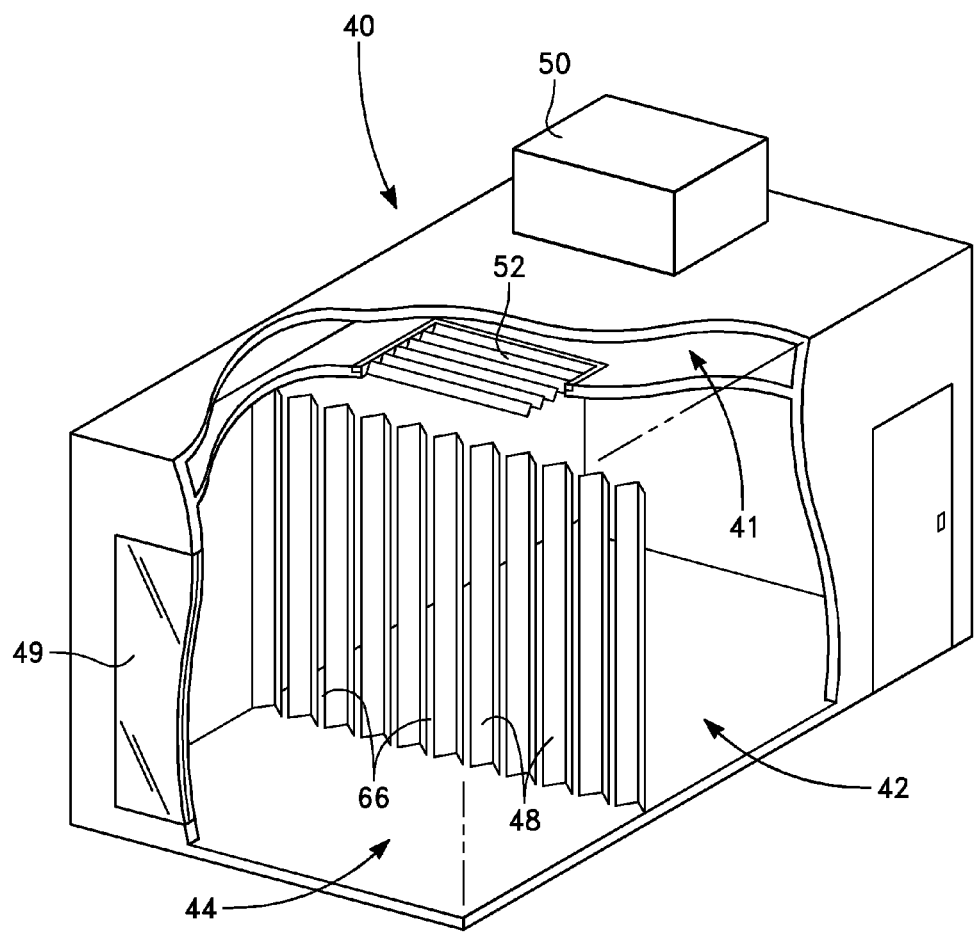
FIG. 21 shows a cutaway view of an embodiment of the apparatus, showing relative positions of the flight chamber and processing unit, and a reservoir of chilled air.

A further embodiment is shown as a cut-away diagram in FIG. 21. Unit 40 includes refrigeration plant 50 located externally on the roof of unit 40, which when operating maintains a reservoir of chilled air in plenum 41 constructed over process chamber 42 and flight chamber 44. The chilled air is maintained preferably at a temperature of 2deg C. The chilled air is delivered to one or both of process 42 and flight 44 chambers, depending on mode of operation, via grills 52 and dampers (not shown). It is advantageous to provide the reservoir of chilled air which can be rapidly circulated through flight chamber 44, chilling the bees quickly so that the time required to collect each batch of bees is minimized. The volume of plenum 41 is preferably approximately twice the volume of flight chamber 44. In the embodiment illustrated, passages 66 and openings 48 to flight chamber 44 are provided by vertical polycarbonate, or other translucent sheet material, elements which form a multiplicity of vertical v-shaped baffles. Each of the said baffles presents a wide, preferably 150 mm wide or greater, opening to process chamber 42, the passage through the baffle diminishing so that the opening to flight chamber 44 is preferably 10 mm to 20 mm wide. Illumination to flight chamber 44 is through glazing 49 which in this embodiment comprises double-glazed sliding doors, through which the operator gains access to remove bees. In this embodiment, heaters and fans (not shown) are installed internally in both process chamber 42 and flight chamber 44.

Figure 12:
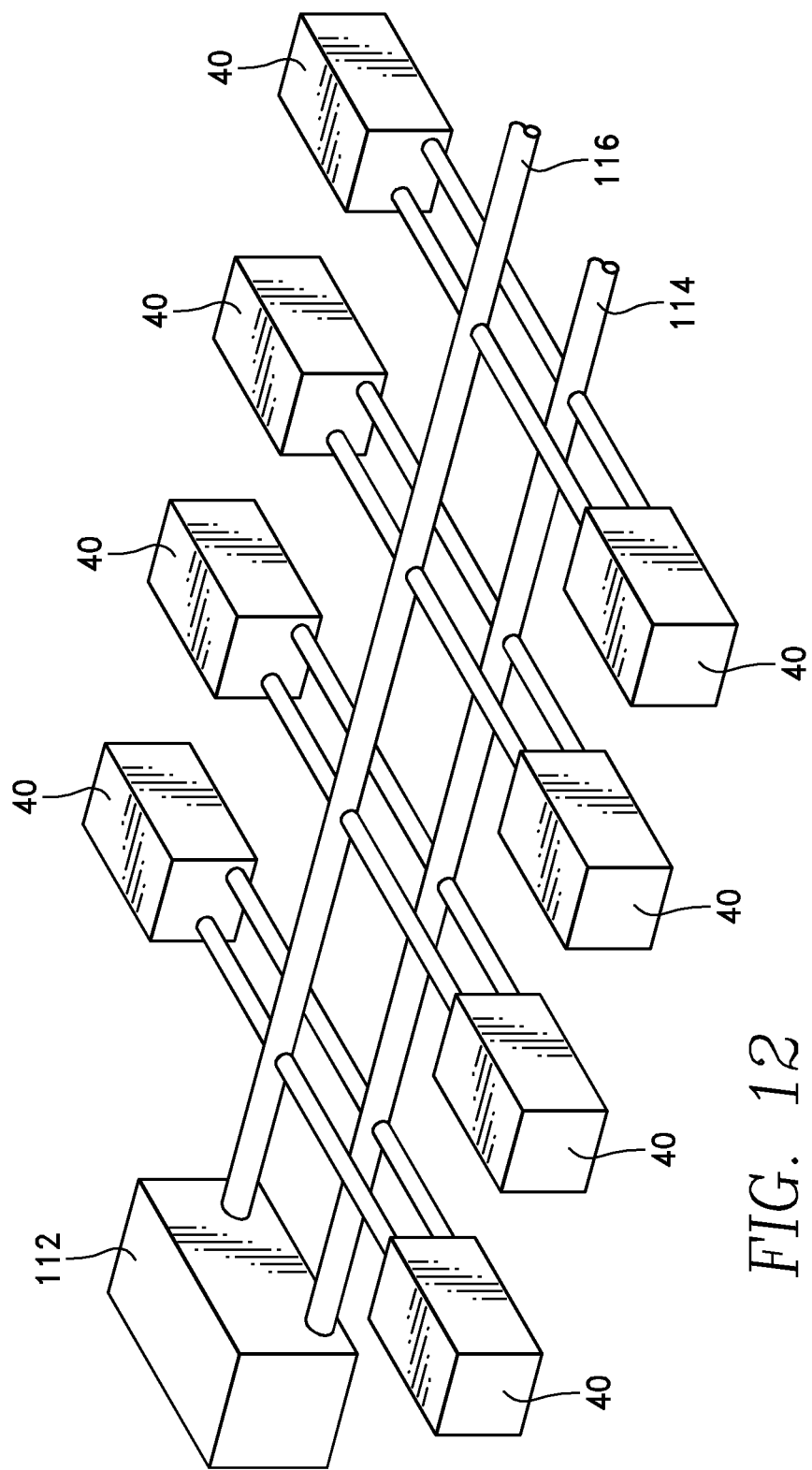
FIG. 12 schematically shows a configuration for utilization of a central plant to provide hot water, chilled water, or refrigerant for a system comprising individual embodiments of the apparatus.
Figure 13:
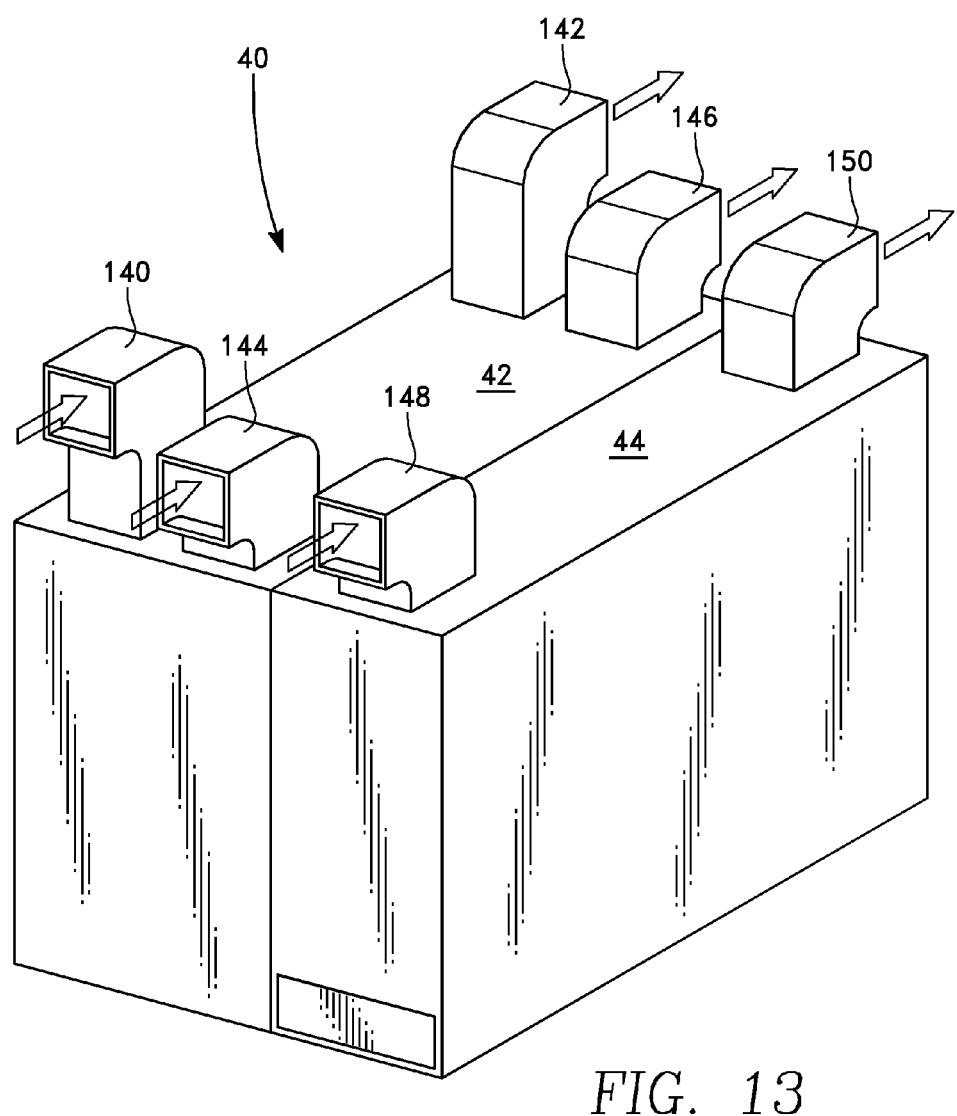
FIG. 13 shows how warm and chilled air may be provided in a central plant and then ducted to individual embodiments of the apparatus.

Embodiments of the apparatus may be installed as complete units, with the unit having its own integrated services, i.e., refrigeration plant, heating plant, humidifier (if required) etc. However, where it is planned to install a number of units, whether all simultaneously, or in a sequence over a number of seasons, there may be advantages in the installation of centralized plant. For example, as shown in FIG. 12, hot water and chilled water or refrigerant could be distributed through hot water lines 114 or chilled water lines 116 from central plant 112 to the individual units 40 to supply the appropriate heating and cooling coils. Alternatively, as shown in FIG. 13, the individual units 40 may be equipped with ducting to receive conditioned air from a central plant. In this case air would be supplied through a dual duct system with separate warm and cold air supplies. FIG. 13 shows warm air inlet duct 140 and warm air outlet duct 142 to the process chamber 42; chilled air inlet duct 144 and chilled air outlet duct 146 to the process chamber; and chilled air inlet duct 148 and chilled air outlet duct 150 to the flight chamber 44. The main distribution ductwork is omitted for clarity. Control of the air flows is by conventional dampers which are not shown here. A dual duct system may be necessary, as each unit may have different environmental requirements at different times. For example, for an embodiment comprising two adjacent processing units 42, one may require warm air in order to stimulate the bees inside to emerge, while the other unit may still require cooling, depending on the history of the bees in that unit and the date the target crop needs to be pollinated.

Figure 14A:
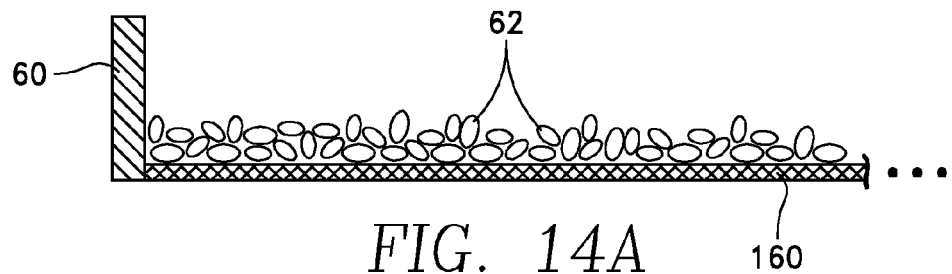
FIGS. 14a-14d show how different nests may be utilized in embodiments of the disclosed apparatus.
Figure 14B:
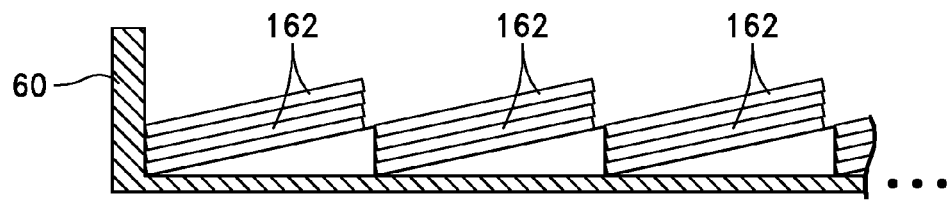
Figure 14C:
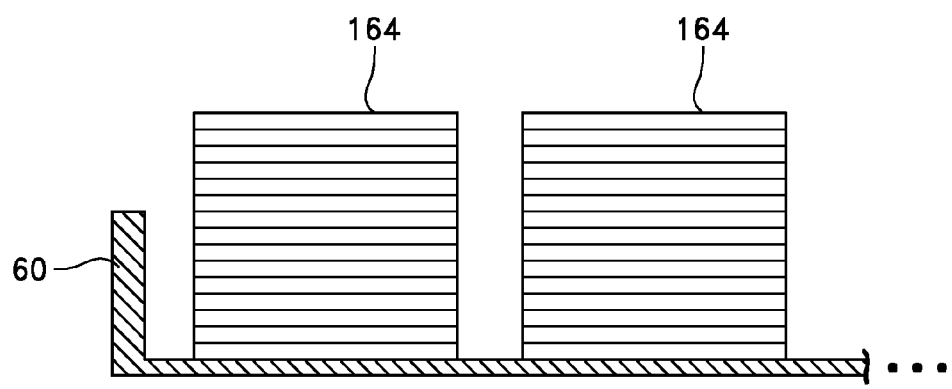

Embodiments of the apparatus are flexible in that the apparatus 40 can accommodate bees in any of the nests described in the introduction, or bees in various nest components, or loose cocoons, or indeed combinations of these, which are indicated in FIGS. 14A through 14C. Each of the nests shown in FIG. 14 has advantages and disadvantages. The effect of the volume required inside the processing unit 40 may be a factor, because that will have an effect on the capital and running cost of the equipment, which will have some influence on the operator's decision on how to handle the bees. The following paragraphs examine the relative packing density of various methods of handling bees.

Figure 14D:
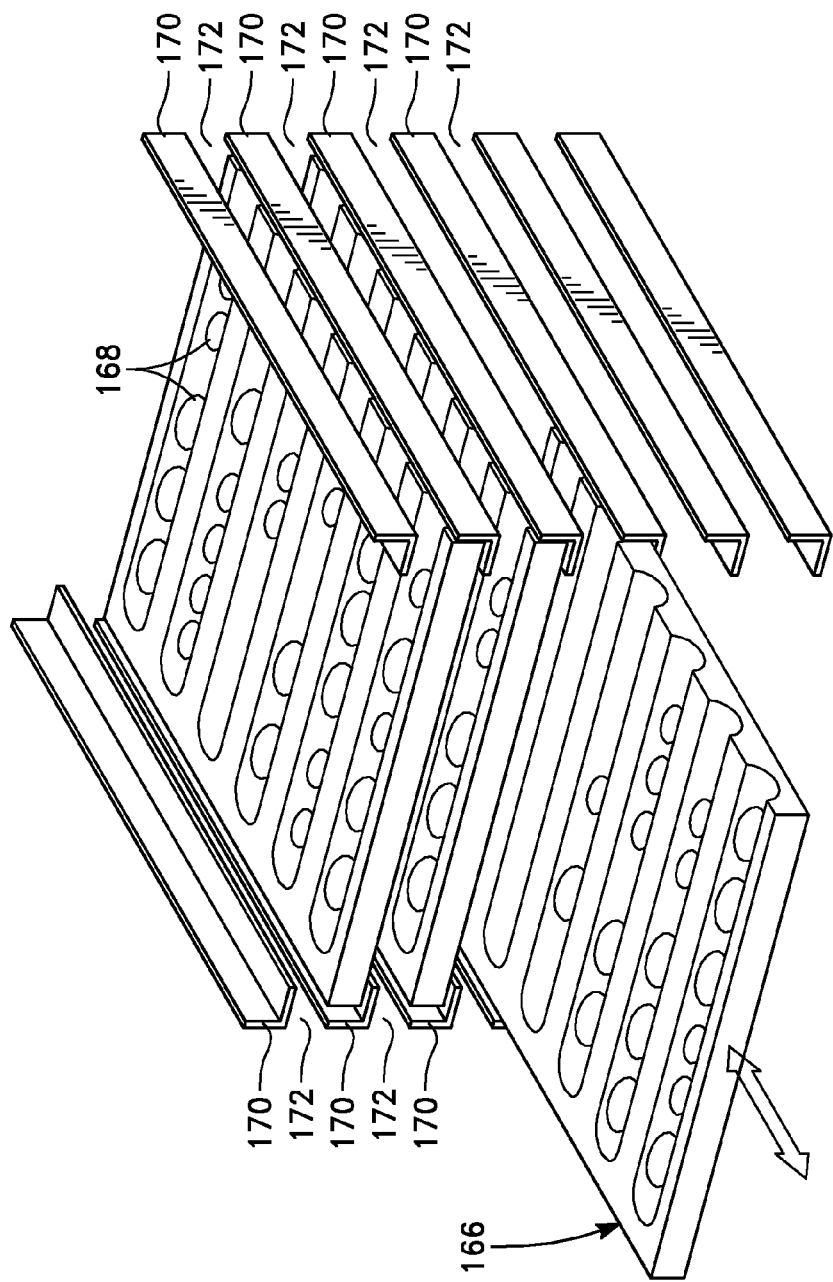

The volume required to house the bees in a particular embodiment of the apparatus will depend upon the way in which the bees are placed into the processing chamber of a particular unit. For example, the bees may be contained within loose cocoons 62, removed from nests, as shown in FIG. 14a. For loose cocoons it is suggested that tray 60 has a mesh base 160. Alternatively, the bees may be contained within cocoons within part of the nest (eg paper straws 162 removed from blocks or outer tubes) as shown in FIG. 14b. It is suggested that the straws or cardboard tubes 162 are stacked in layers at a slight angle of say 10 deg to avoid the tube entrances being blocked by adjacent tubes. If the angle is significantly greater than 10 deg, the nest debris tends to accumulate towards the base of the tube as each successive bee emerges, causing an obstacle for the last bees to emerge. As yet another alternative, the bees may be contained within cocoons within complete sealed nests 164 as shown in FIG. 14c. The figure shows a sheet type of nest, but any known nest can be used in the invention. As yet another alternative, the bees may be contained within cocoons within complete but opened nests, as shown in FIG. 14d.

To compare the implications of the method of placement within the processing chamber of embodiments of the apparatus, the following table gives an indication of the volume necessary for storage of 1 million cocoons. In each case allowance is made for the airspace necessary for sufficient airflow to warm or cool the bees, and allowance is made to mitigate the deleterious effect of close packing on loose cocoons and the consequent build-up of metabolic heat.

|  | volume to hold 1 million bees | Advantages | disadvantages |
|---|---|---|---|
| loose cocoons | 3.1 m$^3$ | Most efficient use of plant space. Enables parasite and quality control. | Costs involved in removing cocoons. More handling of bees - possible damage to bees. Mechanisation required. |
| Cocoons in straws | 3.8 m$^3$ | Efficient use of plant space. Relatively easy to examine contents. | Handling required to move straws from tubes. Nest materials more expensive. |
| Cocoons in cardboard tubes | 5.9 m$^3$ | Handling of nests is simple and unskilled. | Difficult to sample or examine contents. |
| Cocoons in tray nests | 5.7 m$^3$ | Handling of nests is simple and unskilled. | Less efficient use of plant space. |
| Cocoons in open tray nests | 10.9 m$^3$ | Arrangement allows most efficient escape of bees from unit. Enables visual examination for parasite and pathogen control. | Least efficient use of plant space. |

As shown in FIG. 14a and the table above, the most effective utilization of plant capacity relies on storage of loose cocoons 62, i.e., cocoons which have been removed from the nests. If this procedure is chosen by the operator, then selection of the appropriate nest type and method of emptying is of great importance. While small scale operations can be carried out by hand emptying of nests, such as tearing or cutting open straws, reeds or tubes, this is impractical on a large scale. On the commercial scale, nests which can be easily opened and mechanically emptied are to be preferred. When calculating the capacity of the plant, it is assumed that open trays of loose cocoons 62 are used, with the cocoons in a layer no more than 15 mm deep, with a substantial air space above for circulating cooling or warming air. The trays may have a mesh base 160 as shown in FIG. 14a to ensure that warmed or chilled air reaches the lowermost cocoons in the layer. The cocoons 62 may be mixed male and female, or it may be preferred to separate the males and females so that different procedures can be applied to each for optimal processing.

The known types of nest for solitary bees include various types which incorporate an inner paper lining tube 162 or straw. The outer holders may be drilled blocks of wood, cardboard tubes, or other material with formed cavities in which the paper liner 162 is placed. In order to make best use of plant space the paper liners 162 may be removed from the outers and placed in racks or holders for efficient placement within the chamber. A suggested arrangement is shown in FIG. 14B which makes stacking of the liners easy, and avoids large numbers of liners falling over. The disadvantage of this method of loading the chamber is the labor involved in removing the paper liners 162 from the outers.

Alternatively, instead of withdrawing paper liners 162 from cardboard or similar tubes, it is possible to stack the complete tubes in racks. The advantage is that no labor is spent removing paper liners; the disadvantage is that the space used inside the chamber is greater.

Another alternative is to utilize tray-type nests 164 as indicated in FIG. 14C. Many versions of tray-type nests are known in the industry. These may be slotted boards of various materials which stack to form an array of U-shaped cavities, or they may comprise formed components which align when stacked to form circular cavities. Nests of this type may be loaded into the chamber with no other handling. This process involves the minimum of labor, and the least involvement of skilled personnel. The shelving or supports may be arranged so that whole nests are slid on guides into the chamber, one after another.

As yet another alternative, tray-type or clamshell nests, or other openable nests may be utilized so that cocoons 168 are exposed, as shown in FIG. 14d. Trays 166 are arrayed in a rack or support 170 such that there is an airway 172 immediately over each tray so that any emerging bee can walk out of the tray 166 and leave the chamber 42, without waiting for bees between it and the entrance of the nest to emerge first. In this way, bees are not kept waiting, for what may be several days, at elevated incubation temperatures while waiting for other bees to emerge and leave.

This tray arrangement is advantageous in that bees are more vigorous when they reach the orchard or place of pollination because they have not used up extra body fat reserves. In addition they are less likely to be dehydrated. A further advantage is that because bees are able to leave as soon as they emerge, they no longer contribute to the mass warming due to metabolic heat production. This process can conveniently be used to examine the nests for predators and parasites, and potentially to treat the nest contents accordingly. For example, mites of the genus *Chaetodactylus* are a frequent and sometimes serious pest of *Osmia* bees. However, these mites are susceptible to dehydration; exposure to dry ambient conditions by opening the nests may be sufficient to kill or greatly reduce the numbers of the mites. The disadvantage of this arrangement is that it is not the most efficient use of plant space. The plant designer must make allowance for the multiple airways that are required for this arrangement, and ensure that (a) the fans and motors are selected capable of providing sufficient pressure to move air along multiple narrow parallel passages and (b) that turning vanes are effectively used to direct approximately equal amounts of air along each airway.

Figure 15A:
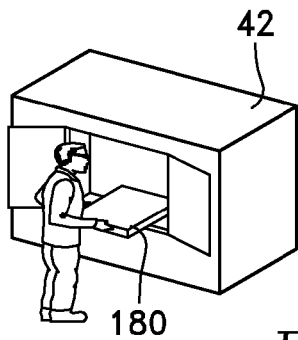
FIGS. 15a-15c show various options which may be utilized for loading bee nests in embodiments of the disclosed apparatus.
Figure 15B:
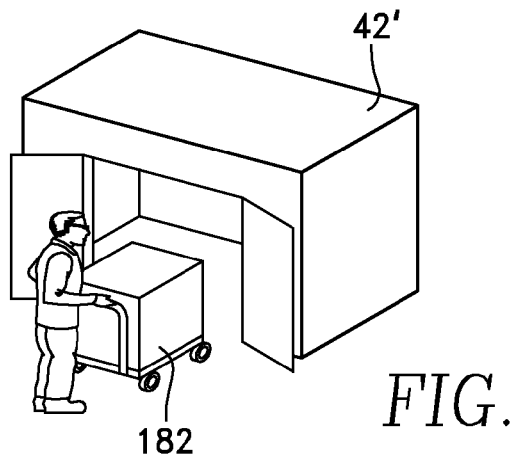
Figure 15C:
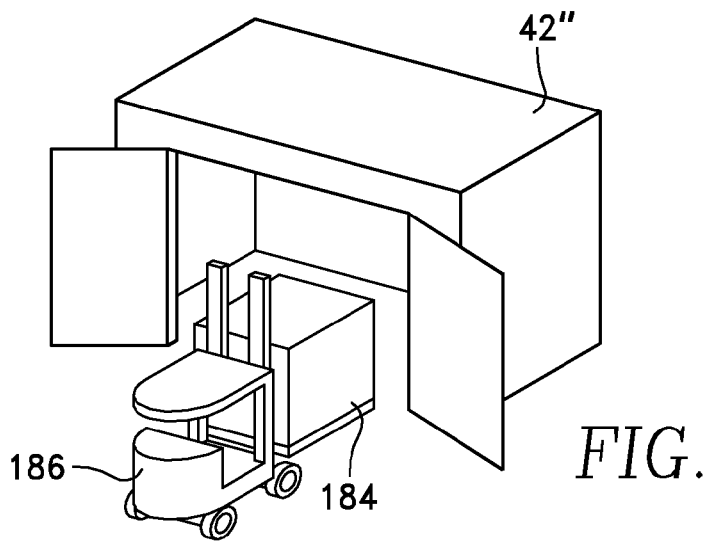

Embodiments of the process chamber 42 may be physically arranged in many ways, as shown previously. Whether the bees are to be placed into process chamber 42 as loose cocoons or within at least one of the nest components described above, there are options for loading the bees in the process chamber 42. FIGS. 15A through 15C illustrate various options. For example, as shown in FIG. 15A, trays 180 of cocoons can be moved from the processing area where they have been removed from nests, and the trays manually placed into process chamber 42, preferably onto a rack or support. In a similar way, the nests or nest parts containing the cocoons may be placed in racks or trays which are transported to the Unit and then placed into process chamber 42 as shown. A further option is to place the trays 180 of cocoons or racks of nest parts on trolleys 182, which are wheeled into process chamber 42' and left in situ. Alternatively, pallets 184 or racks of nest parts may be lifted and placed in the process chamber 42" by fork lift 186, or wheeled into the chamber using a pallet jack. These alternative methods of loading embodiments of the processing unit drive labor costs down.

Embodiments of the apparatus provide the appropriate environmental conditions for the bees throughout several stages of their lives. At some points—for example during the prepupal period, embodiments of the apparatus may provide heating. At other points, for example during the winter diapause, embodiments of the apparatus may provide cooling. The heat transfer is by warmed or cooled air, which is distributed in an even, slow-speed air stream, which will be described more fully later. Acceptable dimensions for air spaces have been found to be:

above loose cocoons—50 mm (+12 mm clear headroom in tray)

above stacked paper liners or stacked tubes—75 mm above sealed nests—25 mm; on each side of sealed nests—50 mm above each open nest tray 10 mm.

The air flow speed is preferably slower than 2.0 m/s and more preferably in the region of 0.5 to 1.0 m/s.

Figure 16:
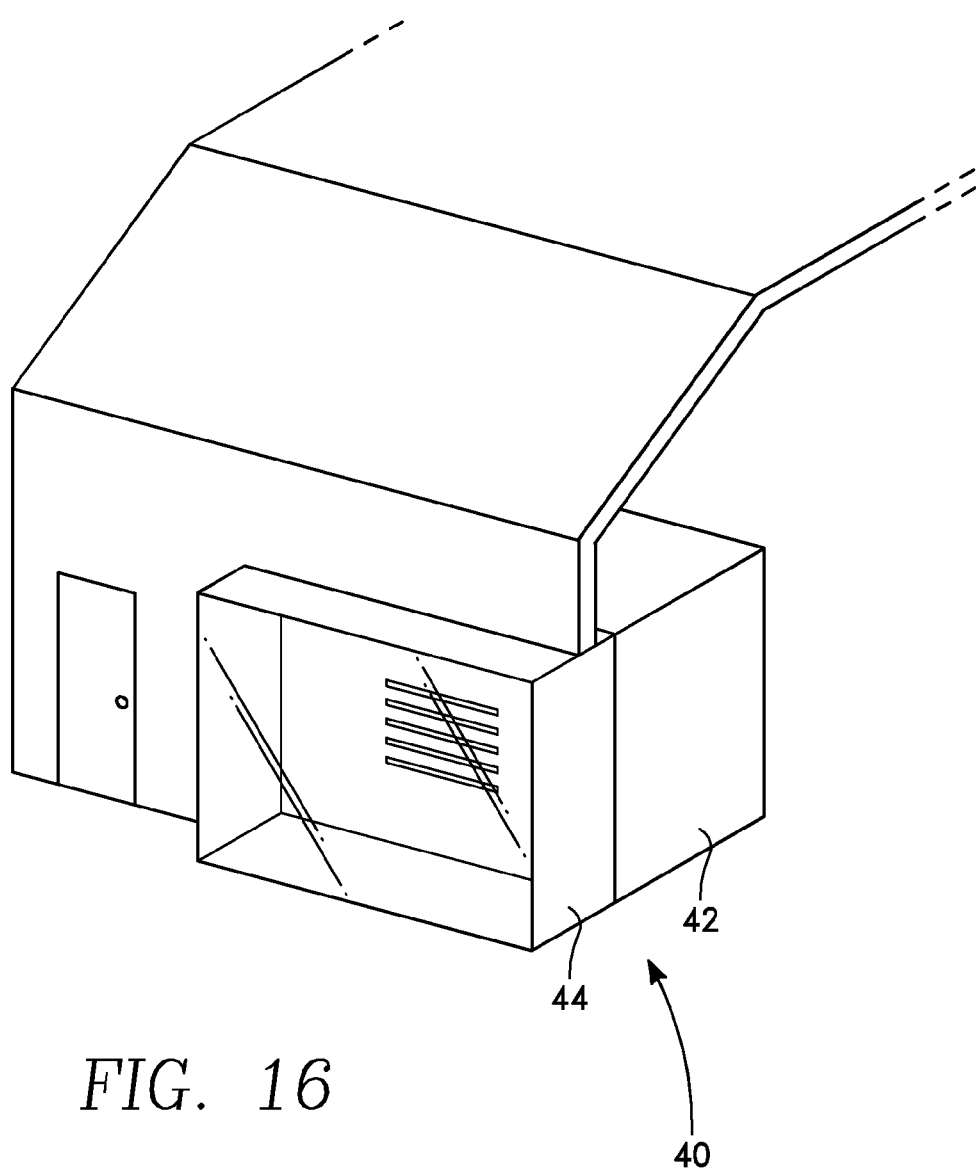
FIG. 16 shows an embodiment of the disclosed apparatus partially located outdoors, utilizing natural light for illumination.

Flight chamber 44 is in its simplest form a chamber bounded by net or glass or other transparent material such as clear plastic, through which bright illumination can be directed. The flight chamber 44 is adjacent to the process chamber 42 and is constructed in such a way to minimize the ability of bees to escape from it. FIG. 3 shows a cross-section of one embodiment of a flight chamber 44. The flight chamber 44 may be permanently fixed to the outer wall of the process chamber 42, or it may be removable, for cleaning, and/or access to remove bees. Escape passages 66 connect process chamber 42 to flight chamber 44. Bees emerging in the process chamber 42 are attracted by light from the illumination means 58 which may be artificial lighting as illustrated. In an alternative embodiment as shown in FIG. 16, the apparatus may be entirely or partially out of doors, so that the illumination which attracts the bees from process chamber 42 into flight chamber 44 is daylight. In a further embodiment, the entire unit 40 may be completely indoors, but provision made in the structure of the enclosing building, such as windows or opening doors, to allow daylight to illuminate the flight chamber.

Referring to FIG. 3, during the period of several months when the bees are undergoing development or in dormancy, the escape passages 66 are not in use, and may allow warmed or chilled air, depending on the current functioning mode of Unit 40, to escape from process chamber 42. To avoid this inefficiency, means for closing the escape passages 66 may be fitted. These may be hinged doors or flaps, or flexible material pressed into the passages, or other means.

The plant may be capable of producing varying temperatures in flight chamber 44 when in use. For the majority of the time during the emergence period, the temperature in flight chamber 44 is required to be at or close to the temperature inside process chamber 42 (say 28deg C.) in order to ensure that the bees leave process chamber 42. Periodically, however, the temperature in flight chamber 44 may be dropped rapidly by directing a cold air stream through the flight chamber. In order to avoid flight chamber 44 being excessively warmed during this process, and process chamber 42 being excessively cooled, escape passages 66 should be of limited area and relatively long so that the effective internal boundary layer within escape passage limits the free movement of air from process chamber 42 to flight chamber 44 and vice versa. In one embodiment, the escape passages are 8 mm high or less and 50 mm long or more. Since cold air will be delivered to flight chamber 44 at the same time as warm air is being delivered to process chamber 42, insulation 94 may be applied to the process chamber 42 as shown in FIG. 6.

In practice the design of escape passages 66 will entail a compromise between providing sufficient space to enable a large number of bees to pass through in a short time, and providing a limited space to reduce heat transfer between the two chambers. Operation of prototype apparatus indicates that bees are strongly drawn towards daylight and rarely return through escape passages 66 to process chamber 42 even when there are no obstacles to prevent their return.

The chilled air stream is preferably at 4deg C. to 8deg C. As shown in FIG. 2, the chilled air stream may be blown into flight chamber 44 through a grill 52 or other delivery device. The chilled air may be provided by a fan and cooling coil dedicated to that specific unit, or cold air may be ducted to each of a number of Units from a central plant room as shown in FIG. 13. In order to bring the temperature of flight room 44 back up rapidly after chilling, warm air may be blown through the same delivery system. Alternatively automatic baffles may operate to divert a portion of the warm airflow normally passing through process chamber 42 into flight chamber 44.

It should be noted that all grills and air inlets and outlets should be fitted with screens to prevent bees entering areas where they are not intended to have access.

During operation, the time required to chill bees in flight chamber 44 sufficiently so that they become immobile and drop into collection means 54, may be of the order of one to ten minutes. The frequency of chilling may be of the order of once every 30 minutes, or a few times a day, but will be determined by the operator on the basis of how rapidly the bees are emerging, and the demand to get them to the pollination site. During the early and late stages of emergence, it may only be necessary to remove bees once or twice a day.

The illumination which attracts newly emerged bees from the process chamber 42 into the flight chamber 44 may be natural daylight, or artificial light 58 as shown in FIG. 3. It should be noted that the illustration of illumination 58 shown in FIG. 3 is merely figurative, and is not meant to indicate the type or number of light fittings to be used. In the case of artificial illumination, the operator has a number of options on how to utilize illumination 58. For instance it may be left on 24 hours per day so that there is a steady filling of flight chamber 44 day and night, which may require staff to be on hand around the clock to handle the bees. Alternatively, illumination 58 may be turned off at night, so that when it is switched on in the morning, a large number of bees will emerge from process chamber 42, requiring quick handling. A further option is to control illumination 58 so that it switches off when flight chamber 44 is being chilled, allowing staff to deal with the collection of chilled bees inside flight chamber 44, without flying bees coming out of the escape passages 66. To enable staff to carry out work within flight room 44 while bees are present, illumination 58 described above may be turned off and red light of a frequency which the bees cannot perceive be utilized instead. In this light the bees will not be active, enabling work to be carried out without disturbance to the staff and without bees escaping.

FIG. 3 shows an embodiment of a collection means. This embodiment includes one or more trays 54 on the floor of flight chamber 44. When the bees are chilled by the cold air stream, they drop into trays 54. The staff then access the trays by, for example opening doors 56 and lifting trays 54 out, replacing them with empty ones, or sliding them out through an appropriate opening, or by any other convenient method. When trays 56 are removed the bees must rapidly be transferred to a cold room at say 6deg C. to prevent the bees becoming active as they warm up and escaping.

Alternative collection means may be by vacuum means, using a modified commercial vacuum cleaner. To avoid injury to bees, the bees should be drawn through a smooth, not corrugated, tube, and the bees should be discharged into a large container in such a way that the velocity of each bee drops as it enters the container, the trajectory of each bee being such that harmful impact with surfaces is avoided.

Alternative collection means are illustrated in FIGS. 17A through 17C. For example the bees may drop into a hopper 190 which may be emptied into a container 192 or containers by opening the base 194 of hopper 190 and letting the torpid bees drop out. In a further embodiment, hopper 190 may deposit bees onto a conveyor belt 196 which automatically transports the bees into containers or direct into a cold room. Various degrees of sophistication and automation may be applied to this and other aspects of the apparatus depending on the scale of the operation.

In a further embodiment (not illustrated), flight chamber 44 may be provided with means for removing parasites and parasitoids such as, but not exclusively, wasps of the genus *Monodontomerus*. The removal means may incorporate a mesh or grill, the openings of which are too small to permit bees to pass through, but through which the wasp can freely pass. The wasps are attracted through the openings by an ultra-violet or other lamp which may be constantly or periodically illuminated. Once the wasps have passed through the openings they may be killed by conventional means such as electrocution or drowning.

Figure 18:
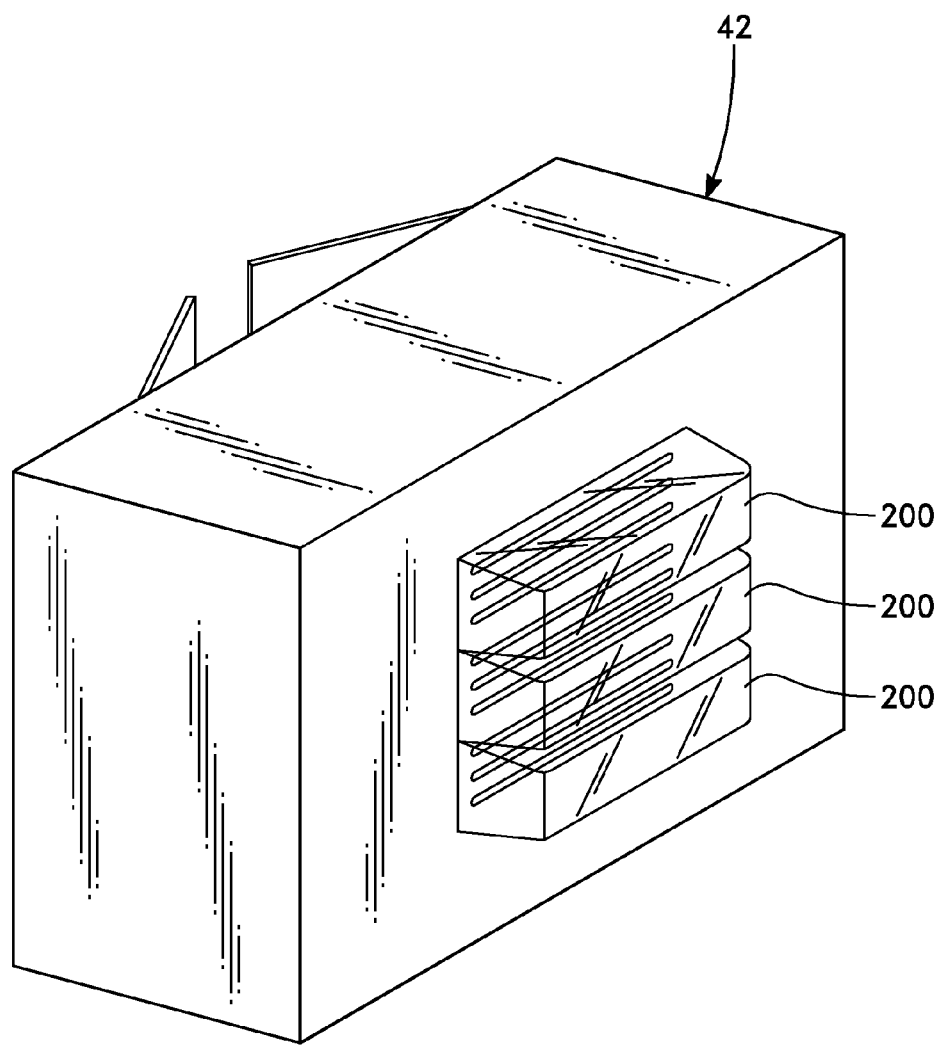
FIG. 18 shows an embodiment of the apparatus which comprises a plurality of removable flight chambers.
Figure 19:
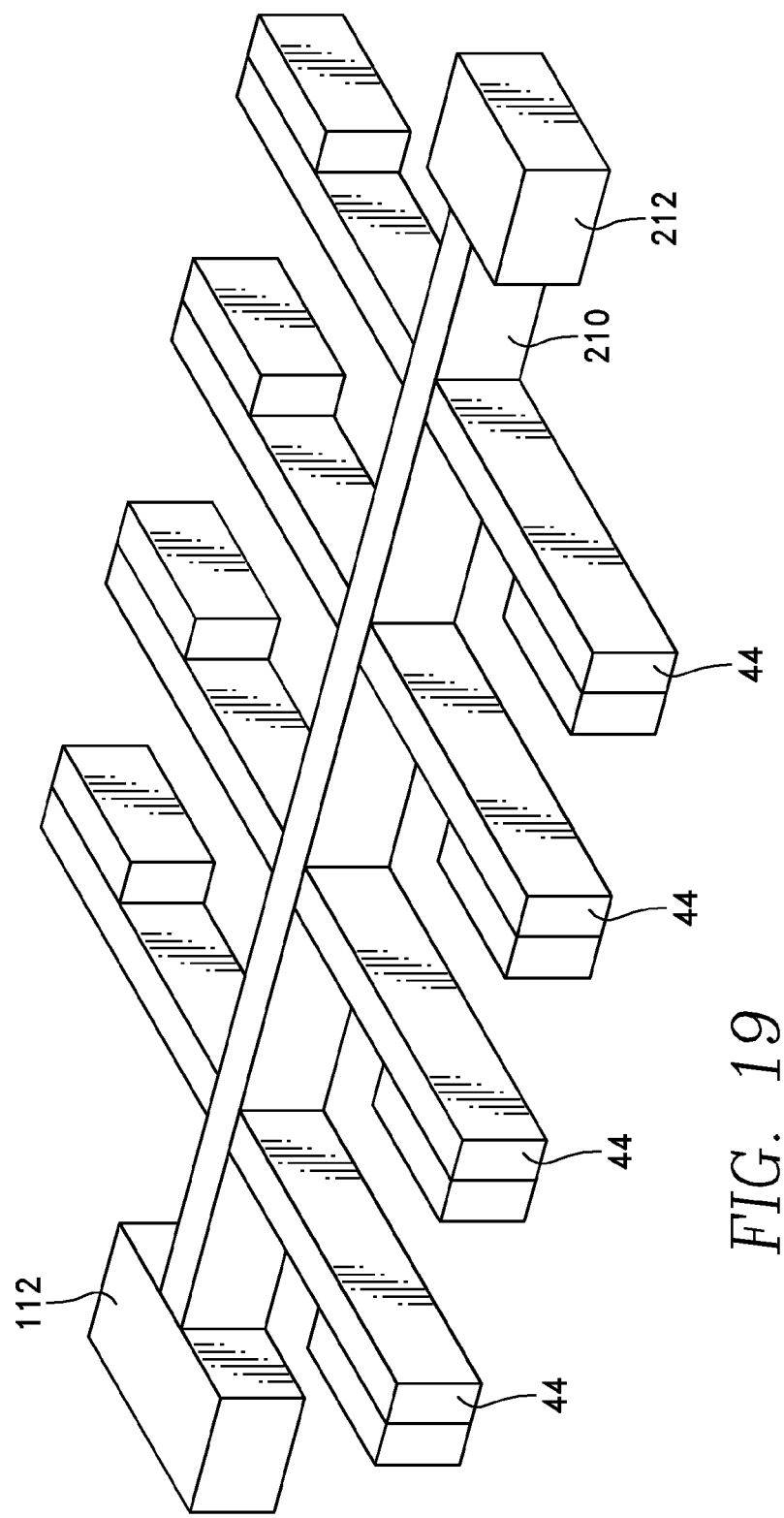
FIG. 19 shows an embodiment of the apparatus which comprises a plurality of extended flight chambers.

In a further embodiment, flight chamber 44 may be fitted with directable air jets which can blow immobile bees from surfaces into collection means. In some circumstances, staff may brush immobile bees from surfaces. In an alternative embodiment flight chamber 44 may comprise a number of smaller removable chambers 200 as shown in FIG. 18. These removable chambers 200 may be individually removed by hand from the wall of process chamber 42, sealed and placed inside a refrigerator or cold room to render the bees contained torpid. At the time of removing each removable chamber 200, it is replaced by an empty removable chamber 200. These removable chambers 200 may advantageously be washed to remove meconium and dried before replacing back in service. These removable chambers 200 may be made of translucent plastic, and be light and cheap, and may be any volume from say 2 liter to 100 liter. This arrangement may be convenient for a small operation A large-scale plant for handling solitary bees for pollination may comprise multiple processing units. Increased efficiency and reduced operating costs may be achieved by extending flight chambers 44 so that they connect into a flight passage 210 as illustrated in FIG. 19. Flight passage 210 is a passage along which the bees can pass in one direction only. In this way all the bees from multiple flight chambers 44 are combined, and they pass into one chamber, denoted chilling station 212, for chilling and collection. For some embodiments, flight chambers 44 and flight passage 210 are not chilled, but maintained at temperatures amenable to bee flight, either by permitting infiltration of air from heated process chambers 42 through escape passages 66, or by active provision of heating if ambient conditions in the facility require it.

Figure 20:
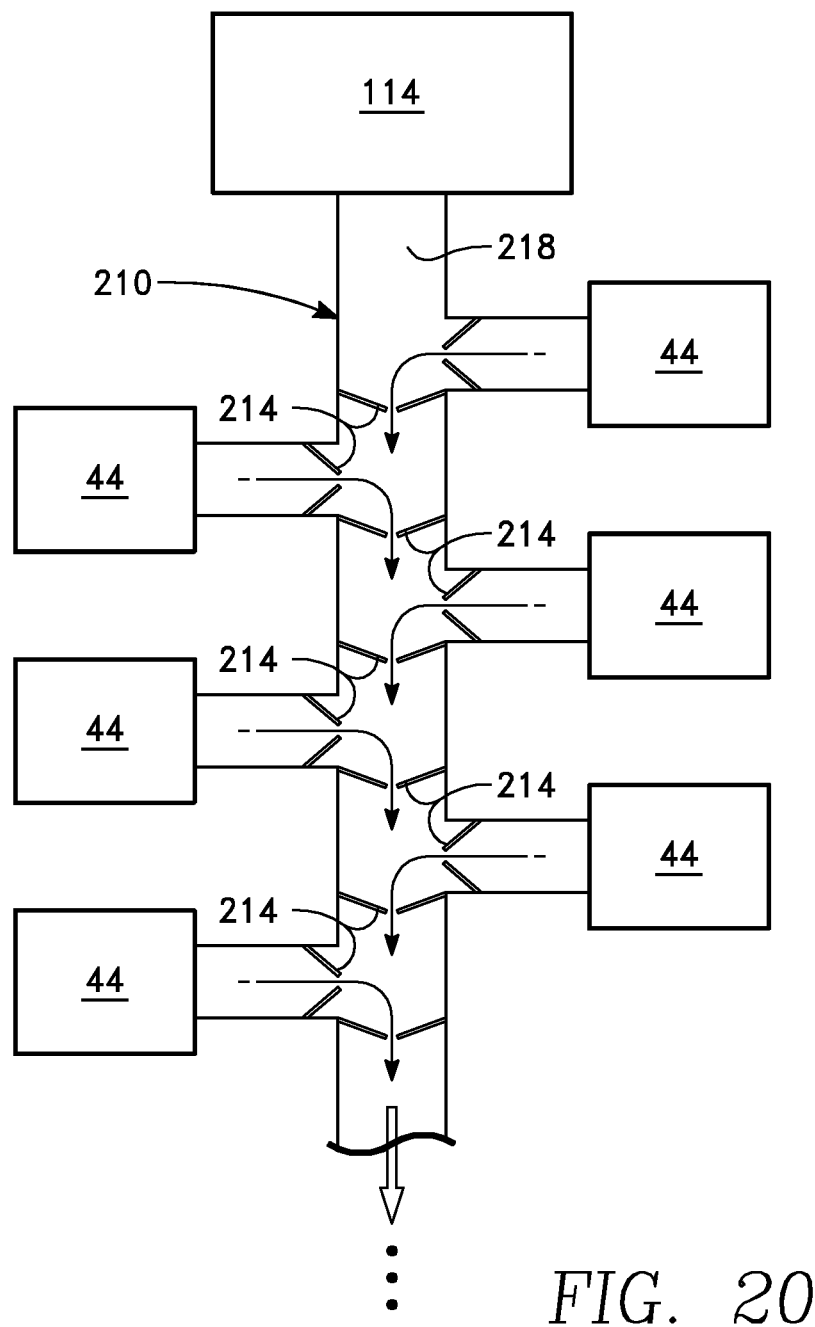
FIG. 20 shows, in plan view, how a flight passage may be divided into zones.

Referring to FIG. 19 and FIG. 20, an embodiment of a flight passage 210 is shown running from plant room 114 towards chilling station 212. Plant room 114 contains the fans, filters and heaters which supply the warmed airflow through flight passage 210 when in operation. In order to direct flying bees in the desired direction, first from each light chamber 44 into flight passage 210, and subsequently in stages along flight passage 210, flight passage 210 may be divided into zones 218 as shown in plan view in FIG. 20. Each zone 218 is separated from the previous zone 218 by baffles 214, where baffles 214 take the form of either horizontal surfaces or vertical surfaces which narrow the passage in the desired direction of flight, acting as funnels.

Each zone 214 may be provided with independent illumination, which can be either bright, or dimmed, or darkened as shown in the following table.

| Zone | 1 | 2 | 3 | 4 | 5 | 6 |
|---|---|---|---|---|---|---|
| Step 1 | dark | dim | bright | dark | dim | bright |
| Step 2 | bright | dark | dim | bright | dark | dim |
| Step 3 | dim | bright | dark | dim | bright | dark |
| Step 4 | dark | dim | bright | dark | dim | bright |
| Step 5 | bright | dark | dim | bright | dark | dim |

The sequence of lighting as shown attracts the bees from a dimly-lit zone to a brightly-lit zone, and moves the bees in stages downstream until they enter chilling station 212 as shown on FIG. 19. Baffles 218 reduce the possibility of any bee inadvertently flying in the wrong direction.

The movement of the bees may be enhanced by the provision of a flow of warm air towards chilling station 212. The effect of baffles 214 on the airflow is to create an area of localized accelerated airflow, in effect creating a nozzle, drawing bees in flight rapidly into the next zone 218 in the flight passage. In addition this makes it extremely difficult for any bee to fly in the reverse direction through the fast airflow between the baffles.

Chilling station 212 may be fitted with means for rapid cooling such as a refrigeration plant capable of providing a substantial flow of chilled air. In one embodiment, the sequence of operations, preferably fully automated, may be as follows:
 1. Bees enter chilling station 212 through one or more flight passages 210, guided by air flow through baffles 214 and sequential illumination of zones 218 in flight passage(s) 210.

2. The airflow in the flight passage(s) 210 towards chilling station 212 is stopped.
3. Final baffles 214 leading into chilling station 212 are closed to eliminate loss of chilled air into the flight passage(s) 210.
4. The flow of refrigerated air into chilling station 212 is commenced.
5. The immobile bees are collected in hoppers, or in open trays, or on conveyor belts, or by vacuum collection, or by any other appropriate means.
6. The flow of refrigerated air is stopped.
7. Baffles 214 are reopened; the flow of warm air in flight passage(s) 210 is recommenced; and the cycle is repeated.

The operation of embodiments of the disclosed apparatus 40 rely upon a thorough understanding of the life cycle of the bee species being handled, and skilled analysis of the state of development of each population being handled. *Osmia* bees and other related bees follow the course of development outlined below. The times given for the duration of each stage are highly variable; those shown below are given only as an indication. In order for the described embodiments to be function optimally, the operator should generate a body of data about each sex of each population of bees being used in the specific area for pollinating specific crops. The life cycle (including the development stages discussed earlier) includes:—egg; larva; prepupa (spinning cocoon); pupa; mature adult; emergence from cocoon; orientation prior to mating; mating; maturation prior to laying eggs (females); period of effective pollination (females); death. The key points for the operator to determine are (a) when does the population reach maturity? and (b) when do bees have to be active in the spring?

Considering the first of these points—when do the bees in a particular population reach maturity?—it is evident that not every bee reaches every stage simultaneously. Apart from the fact that there will be natural variation in the time it takes individuals to develop, there may be a period of over four weeks during which an individual female is laying eggs, so the first eggs laid are likely to mature four weeks earlier than the last eggs laid. If the normally-occurring variation is included, then the individuals in a population may reach maturity over a period of five weeks or more.

The manager or other responsible person may be expected to be skilled in examining the bees, either by opening cocoons and observing the contents, or taking and analyzing X-ray images of bees in cocoons, or by any other appropriate method. A good statistical knowledge may also be advantageous in drawing conclusions on the probable state of the population in general based on observations of relatively small samples. It may be stressed that development and emergence characteristics can vary considerably between populations from year to year, and management decisions are more soundly based on sampling of current populations than relying on data from previous seasons.

Procedures for moving bees from the orchards or fields will vary depending on circumstances and the type of nest in use. There are indications that early larval stages are damaged by rough movement during transport. A larva that has not reached its fifth instar (shedding of cuticle) is immobile; if dislodged from its pollen provision it may starve. It is advisable therefore to leave the nests in the orchards or fields for as long as is practical, consistent with orchard management, presence of parasites, applications of chemicals, etc. If the manufacture of the nests permits it, it is suggested that nests are transported from the orchard or field with the cavities pointing more or less vertically upwards, so that any larvae which are dislodged from the pollen mass on which they are feeding do not fall away from the pollen, but fall back on to it. Some nest designs have entrances facing in multiple directions; these should be loaded onto the truck for transport with the cavities horizontal.

When occupied nests are returned from the pollination location, it is advisable that they are unloaded with a minimum of rough handling, and placed within a secure environment which is dry and safe from predators. Each operator should assess the nature of the risk at each storage location and plan the storage facilities accordingly. For example, if rodents are a hazard, the nests should be stacked on shelving which rodents cannot climb. Chemical-based bait traps for predators should not be placed in or near the storage facilities. Insect killers which contain pesticides should not be permitted within the premises. The storage area preferably will be dark. Black light traps may be utilized as described in Bosch and Kemp to kill parasitic wasps such as *Monodontomerus* species. The bees in the nests will continue their development in the storage area, with the rate of development depending on environmental factors, in particular, the temperature. Daily fluctuations in temperature affect development rate, not only the maximum or average temperature. The operator may allow the bees to undergo a significant proportion of the development in the storage location, or the bees may be transferred quickly to the unit.

For commercial (as opposed to research) purposes, it may be preferable not to remove the bees from the nests until the great majority are fully developed adults with expanded wings, with hardened and dried bodies. At this stage the bees are robust and cope well with the handling involved in removing them from the nests. Optionally, the operator may make the decision to remove the bees from the nests as soon as it is observed that close to 100% have finished spinning cocoons. Although the bees are less robust at this stage, other operational considerations may take priority, and the slight loss incurred by the early handling may be considered acceptable.

When the operator decides it is appropriate to load the bees into the Unit 40, the bees are placed within the process chamber 42 in one of the ways previously described, i.e., either as loose cocoons 62, or in a nest or part of a nest. It is preferable that the particular unit 40 be maintained and tested prior to loading the unit. The unit controls will be set to provide the temperature conditions determined by the operator as best suited to the population of bees in use. Different temperature regimes may be employed at different stages of development to provide rapid development and healthy bees. Regular sampling enables the management of each population to be precise. In order that different populations may be treated in the best manner—for example from early as opposed to late almonds; from cherries or plums as opposed to almonds; from different locations, etc—it is preferable to hold different populations in different process units, which can be independently controlled.

a) Operating the Unit during development. The unit controls are set to provide the conditions most appropriate for development as outlined previously, providing a steady flow of warmed air over the bees or nests. The principal target is to provide rapid development in order that the chilling period is as long as possible. During this development period, the operator will examine samples regularly to determine the rate at which development is taking place. If the operator decides to introduce a period of fluctuating temperatures to induce rapid prepupal development, the date to do so is determined by examining young bees inside cocoons 62. (The operator may decide that this step is an unnecessary procedure and maintain constant conditions throughout development.) The conventional practice is to hold the bees at development temperatures until 100% (or very close to 100%) of sampled cocoons 62 are determined to contain mature hardened adults, then wait for a further period, typically two weeks, before dropping the temperature to initiate winter diapause. The decision on when to drop the temperature in the unit 40 is crucial; if the temperature is dropped too soon, some of the adult bees do not enter diapause properly (indeed some may not be mature adults); if the temperature drop is delayed too long, then bees may use up too much of their body reserves (known as fat bodies) and may die before entering diapause, die in diapause, or emerge too feeble to be effective pollinators. It may be noted that the ambient temperatures (particularly in California conditions) during the later stages of development may be higher than desirable for healthy development of the bees and that the controls should be set to prevent the temperatures inside the unit exceeding approximately 30deg C. by switching from heating mode to cooling mode.

b) Stepping Down Temperature Instead of exposing bees to thermal shock by dropping from say 28deg C. to say 4deg C. in one step, it is suggested that the temperature reduction is carried out in a series of increments of say 5deg C. every three days, or say 2deg C. every day. This may be done manually by the operator or programmed to take place automatically. It may be noted that typically with bees used in almond pollination in California, the date for dropping the temperature occurs in July or August, i.e., when ambient temperatures are highest. These maximum cooling loads should be calculated and the unit designed with a plant capable of delivering the necessary performance.

c) Operating the Unit During the Overwintering Period The controls are set to maintain a constant temperature of preferably 4deg C., although operators may optionally choose to run the unit at 0deg C. to 7deg C. It may be advantageous to provide periodic 'spikes' of high temperature to say 20deg C. during the overwintering period.

d) Stepping Up Temperature The decision-making process on when and at what rate to warm up the bees to induce emergence from cocoons 62 is described more fully later. At the date decided the temperature may increased in one step, from say 4deg C. to say 28deg C., but more precise control of emergence can be achieved by raising the temperature in stages, for example to 12deg C. for one week, to 20deg C. for a further week, then to final incubation temperature of say 28deg C.

e) Operating the Unit During Incubation and Emergence Initially the unit should be set to run at a predetermined temperature, say 28deg C. The purpose is to stimulate bees to emerge on target dates. These target dates will not be fixed, because the flowering of the trees may be pushed forward by fine weather and held back in adverse weather. The operator therefore can speed up emergence or delay it, by adjusting the temperature within the process chamber 42. The prolonged periods of step-up temperatures make the bees more sensitive to the manipulation of emergence by adjustment of temperatures. The closures, if provided, on the escape passages 66 must be opened or removed and the illumination 58 allowed to create bright conditions in the flight chamber 44. As each bee emerges, it is attracted towards the light and crawls through an escape passage 66 into the flight chamber 44. Typically each bee rests for a short time, then voids the meconium which has been stored in its intestine during the duration of its time inside the cocoon. In the enclosed conditions of the flight chamber 44, bees fly for only a short period, then come to rest on a wall or floor, or, if provided, a roosting area. At regular intervals, either under manual control or automatically (either timed, or when electronic counters indicate that sufficient bees have entered the flight chamber 44), a chilled airflow is allowed to circulate in the flight chamber causing the bees to become inactive. They may fall, or be blown, or brushed manually or automatically in collection devices as described earlier, and then transferred to cold storage or transported directly to the orchard or place of pollination. Numerous embodiments are described later.

f) Operating The Flight Passage In the embodiment where multiple units 40 are linked to a flight passage 210 as discussed above, the bees are not removed from the flight chamber 44, and no chilling is provided to the flight chamber. Instead the flight chamber 44 is maintained at or slightly below the temperature of the process chamber 42, either by supplying warmed air to it, or passively by the leakage of warmed air from the process chamber through the escape passages into the flight chamber. Each flight chamber 44 is connected at one end to the flight passage 210 by a baffle. The flight passage 210 is maintained at a temperature of 20 to 28deg C. by a strong airflow which moves in the direction of the chilling station. Bees active in each flight chamber 44 are attracted towards the flight passage by periodic switching of the illumination 58 in the flight passage 210 from off, to dim, to high. Once through the baffle between the flight chamber 44 and the flight passage 210, each bee is attracted downstream by the regular sequencing of lights. When a bee approaches the baffle 214 between zones of the flight passage, the airflow accelerates rapidly, dragging bees through the gap. Each bee passes through a sequence of zones, until it passes through the last baffle 214 which opens into the chilling station. When the operator makes the decision to manually operate the chilling station 212, or it is operated automatically after a time interval, or it is operated when bee detectors have sensed a certain number of bees have entered, the flow of air along the flight passage 210 ceases, or is diverted to by-pass the chilling station. Simultaneously, the baffle 214 between the flight passage 210 and the chilling station 212 is closed. After chilling has taken place in the chilling station 212, the baffle 214 is reopened, and the flow of air recommenced or redirected back towards the chilling station 212.

g) Operation of the Chilling Station The chilling station 212 functions in a similar manner to the flight chamber 44. While the bees are accumulating in the chilling station 212, the temperature in the chilling station is maintained at reasonable flight temperatures by the warm airflow from the flight passage. When chilling commences, a large amount of cool air at say 6deg C. or lower is rapidly passed through the chilling station 212, causing the bees to become inactive and drop into collection means. The subsequent handling of the bees is as described previously.

The unit 40 may comprise various exterior displays which can be observed by anyone in the vicinity: Air temperature entering process chamber; Air temperature within process chamber; Air temperature leaving process chamber; Humidity within process chamber; Air temperature within flight chamber; Air temperature within flight passage (if installed); Air speed within flight passage; Air speed between baffles of flight passage; Air temperature within Chilling station (if installed). Where multiple units 40 are installed, these readings should be available for each unit. In addition, these readings may be remotely accessible, for example on a computer within the same building, or from a remote computer connected online or via a cellphone network.

It would also be a useful tool for the operator to insert a thermometer probe within the bees—either within the layer of bees where loose cocoons are stored, or within a nest where nest components are stored—in order to be aware of the temperature that the bees are experiencing. During normal operation this will be close to the air temperature, but in the early stages of chilling or warming, and more critically in the case of power or plant failure (see below), the temperature within the bee mass will lag the changes in air temperature.

Rapid warning of unplanned operating conditions is advisable, and it is suggested that visible and audible alarms are installed within the premises to warn staff of the following issues: Too high or too low air temperature within or leaving the process chamber; Too high or too low air temperature within any of flight chamber, flight passage or chilling station; Power failure; Systems failure Preferably systems are also in place to remotely and automatically alert persons in managerial positions of the above circumstances by cellphone or internet.

The storage and care of bees is crucial to the viability of the business, and safeguards should be built into the systems. For example, back-up plant should be installed so that in event of the failure of a component or a system, then automatic changeover takes place to ensure that the required environmental conditions are maintained. The precise arrangement of back-up systems will depend on the scale of the operation and the design equipment. Many arrangements of back-up systems are known in the field of refrigeration and air-conditioning; illustrations are given in the following table.

| Type of installation | |
|---|---|
| Refrigerated container | Parallel identical electrically-powered systems are installed; on failure of one system, the second is switched on. |
| Refrigerated container | An electrically-powered system is the normal method of operation; a parallel diesel-powered system cuts in in case of power failure or first system failure. |
| Central plant | Stand-by generator cuts in on power failure. |
| Central plant | Duplicate plant components may be provided which can be brought into operation in the case of failure of the duty component; for example<br>Two or more compressors<br>Multiple condensers<br>Duplicate pumps<br>Multiple evaporators |
| Central plant | A complete duplicate system. |

The nature of the risk of plant failure should be understood by the operator. Where a cold room or other chilled chamber loses refrigeration, it may be days before the internal air temperature rises to levels which would adversely affect the performance of the bees by breaking the winter diapause. In the natural environment, overwintering bees are certainly are exposed to unusually clement periods, so it should be understood that a brief spell of warmth is not a serious hazard.

To avoid catastrophic loss due to fire, earthquake, malicious damage, flood, epidemic disease and severe parasite and predator attack, isolated plants should be established, as soon as the operation is large enough to justify the capital and running costs. In this way the risk of severe loss is limited to one plant out of two or more. Precautions should be taken in line with conventional biological management practices to prevent transmission of infectious material from one location to another.

Because the cocoons contain living animal material, there is a demand for oxygen to enable respiration to take place. The air supply system therefore cannot be a totally recycled air system but must make allowance for a proportion of the air passing through the system to be fresh. The same proportion of used air must be simultaneously discharged. The fresh air requirement could be met by ensuring that the process chamber 42 is not airtight, and that leakage provides for sufficient fresh air, but it is suggested that the design of the unit 40 should allow for accurate replacement of stale with fresh air. (Conventionally this is provided by interlinked recycle/discharge/inlet dampers which can be set to one position or controlled.) The oxygen requirement of 1 million females varies at different stages of development and activity. The table below indicates the varying oxygen demand, and the minimum amount of fresh air that consequently needs to be drawn into the process chamber 42.

| Stage of development or activity | Oxygen demand for 1 million females Liters per hour | Fresh air demand for 1 million females Liters per hour |
|---|---|---|
| Larva | 100 | 475 |
| Prepupa | 30 | 140 |
| Pupa | 20 | 95 |
| Overwintering adult | 30 | 140 |
| Emerging adult | 320 | 1,520 |

Conventional air conditioning design will be applied to the calculation of heating and cooling loads. In addition to normal heat gains and losses, the contribution of the metabolic heat generated by the bees should be taken into account. This heat is directly related to the oxygen consumption and is tabulated below.

| Stage of development or activity | Metabolic heat production of 1 million females |
|---|---|
| Larva | 550 W |
| Prepupa | 150 W |
| Pupa | 125 W |
| Overwintering adult | 150 W |
| Emerging adult | 1800 W |

As discussed above, in some methods of operation the cocoons are removed from nests. This enables various treatments to be applied if necessary or desired. For example, it may be convenient for the unit 40 to comprise means for applying disinfectant, either as a mist or by dipping, to prevent the growth of molds, to combat mite infestation or to control other pathogens. The disinfectant may be dilute sodium hypochlorite or another chemical. Disinfection may be conveniently carried out by washing loose cocoons and subsequently placing them on trays 166 and setting the controls to provide air flow conditions which dry the cocoons. Preferably trays 166 are manufactured with mesh or screen bases to enable (a) liquid to drain away and (b) drying air to contact cocoons from the underside. A further option is for the unit 40 to comprise means for exposing the cocoons to ultraviolet light to attack pathogens on the exterior of the cocoons.

The means of application of bactericides, fungicides etc can be incorporated within the process chamber 42.

Bees can be stimulated into activity within the cocoons by physical stimulus, such as pressure, squeezing and movement. The unit 40 may comprise means for imparting motion, such as rocking or vibration to the stored nests and cocoons to provoke more rapid emergence. An alternative method is to provide one or more rotary drums in which loose cocoons are placed. By rotating the drum(s) at a rate of say 1 to 2 revolutions per minute, the bees are subjected to a modest continuous agitation.

During the overwinter period, the air circulating in the process chamber 42 may be chilled, typically to 4deg C., to provide the optimum conditions for the mature adults. This cooling increases the relative humidity. At the same time the bees are respiring, and hence producing water vapor. In the case of loose cocoons in trays 166 and open tray nests, this water vapor is largely transferred to the air circulating in the chamber. (In sealed nests, much of the water produced by respiration is absorbed by nest materials, if porous, and the mud partitions and pollen loads.) In addition, to support respiration, a proportion of fresh air needs to be drawn into the air stream as discussed above. These factors continuously introduce water vapor into the system, thereby maintaining the air circulating in the process chamber 42 at saturation or close to it. While the bees do not appear to suffer from high percentage saturation, this can enhance the growth of molds and increase the survivability of *Chaetodactylus* mites. It may be desirable therefore that the air circulating through the process chamber 42 should comprise dehumidification means to reduce the percentage saturation, preferably to 50%, or whatever level the operator determines is appropriate in the individual circumstances. An additional benefit of dehumidification during overwintering is the reduction of mold growth. Faecal pellets, pollen grains and nest debris coat the exterior of the cocoons, forming a nutritious substrate for the growth of fungi. A certain degree of mold is not harmful to adult bees in cocoons, particularly when it develops near the end of the winter diapause. These molds are adventitious, taking advantage of the environmental circumstances and not specifically targeting the bees. If allowed to spread, mold forms a substantial barrier which prevents newly emerged adults from escaping.

On the other hand, during the development period, air is heated to provide the appropriate conditions, thereby lowering the relative humidity further. It is straightforward by conventional means to humidify the air. The sensitivity of bees to humidity levels during development and overwintering has yet to be accurately determined.

As discussed previously, the illumination 58 which attracts the bees into the flight chamber 44 may be natural daylight or artificial light. Artificial light may be preferable in many operating circumstances, in that bees will remove themselves from the process chamber 42 throughout the 24 hours of the day, whereas if natural light is used, bees will remain within the process chamber for 12 to 14 hours each day. If artificial light is employed, it may be preferable to use lighting with a color spectrum close to natural daylight. If fluorescent lighting is used, a combination of circuits using different phases of a three-phase supply may be advantageous, because the rapidity of bees' vision enables them to perceive the flicker at the alternating current frequency which fluorescent lighting exhibits. This appears to cause them difficulty in controlling their flight. By using three separate lighting circuits on three phases, the flickers effectively cancel out.

The flight chamber 44 is preferably constructed of smooth washable waterproof materials. The normal behavior for newly-emerged bees is to rest for some time and void the waste which has accumulated in their guts during the whole of the period inside the cocoon. In a single unit 40, handling a million bees, several kilograms of this waste, called meconium, will be deposited in a few days of operation. This faecal matter is sticky and if it is permitted to accumulate, can damage bees by adhering to wings and body parts. Provision should be made to enable meconium deposits to be cleaned regularly.

The unit 40 may comprise counting means for counting the numbers of insects passing through passages or through gates. Such devices may be advantageously incorporated in embodiments of the apparatus, for example in the passages 66 between the process unit 42 and the flight chamber 44. This data can be integrated to check that the actual number of bees emerging matches the predicted. This information may be interpreted by the operator who may manually adjust the controls of the unit 40 in order to increase or decrease the rate of emergence of the bees to match the required rate. Alternatively, such devices can be used to control the operation of the chilling chamber, for example, initiating the chilling sequence when a specific number of bees, say 10,000, have entered the chamber.

Bees show preferences when inactive to roost in cavities in clusters of ten or twenty or more. It may be advantageous to provide roosting means or devices within the flight chamber 44. When the bees are chilled for removal, it may be convenient to transfer the roosting devices to the cold room with the bees still in them.

The flight chamber 44 may comprise feeders which provide a dilute sugar syrup; water feeders which supply water; and pollen feeders which supply pollen or pollen substitute or pollen supplement. Bees feed within a short space of time after emergence.

A key element in the success of pollinating using solitary bees is reducing the amount of time between release of bees in the orchard and the time when the females start foraging for food to place in the nests. There is a natural delay because a female must mate, and then wait for a period while her ovaries mature and she can start laying eggs. It would be advantageous therefore if provision could be made for mating to take place before the bees are deployed in the orchard. The flight chamber 44 of the current invention provides that possibility. Embodiments of the flight chamber 44 may be constructed sufficiently large, with provision of a large number of surfaces on which mating bees can rest. Males will attempt to mate within a very short period of time after emerging. It is recommended that the flight chamber 44 be emptied regularly to keep the numbers of males and females within it relatively low; if very large numbers are present, it appears to deter mating. If mating does take place, it is suggested that the bees are subsequently kept at higher temperatures than previously discussed, between 8deg C. and 10deg C.

For the majority of the time, the demand from all units 40 in a bee facility will be similar, i.e., all units will require cooling, or all units will require heating at the same time. However, during the period of preparation for pollination, some units 40 may still be in chilling mode while others are in heating mode. To maximize efficiency, heat may be recovered from the refrigeration evaporators and supplied to the heating circuit. The engineer or designer may specify heat pumps.

Description of Statistical Method for Matching Emergence with Crop Flowering

As described previously, the normal pattern of egg-laying by these bees in the wild is to lay a number, say three females, then follow that with say five males. The males are therefore at the mouth of the nest. The bees respond to temperature cues and will emerge when they have experienced a certain amount of heat over a certain period. In horticulture, entomology and agriculture, the technique of summing degree-days is a well-known and reasonably accurate way of predicting when leaves will appear, when flowers will open, when insects will emerge, etc. The number of days when the temperature exceeds a threshold temperature multiplied by the number of degrees between the threshold and the daily maximum are summed. When the sum reaches the degree-days for that species, then the leaves, flowers, insects etc will appear.

Figure 22:
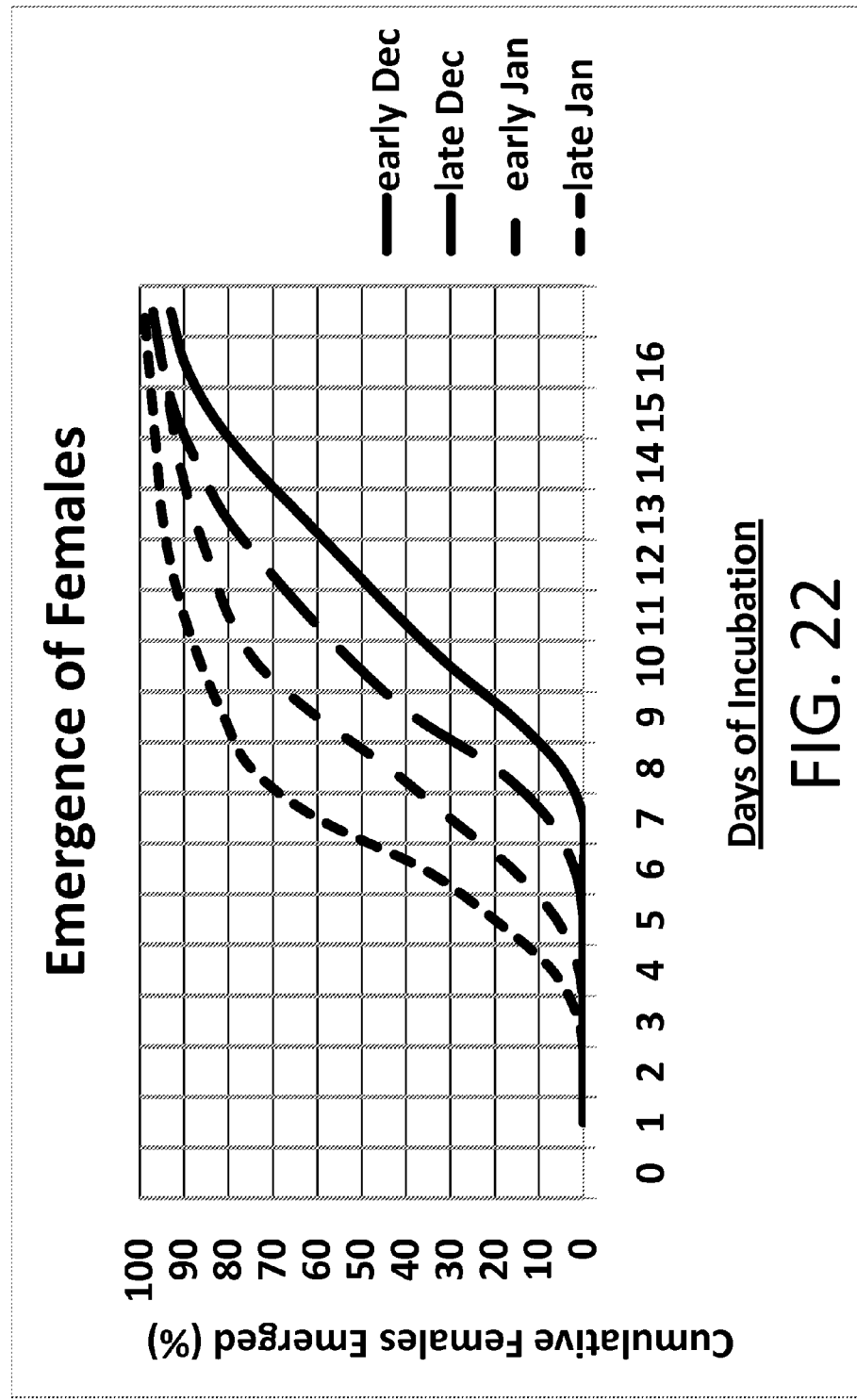
FIG. 22 shows typical emergence data derived from a sequence of four advance trial incubations

In the same way, when the bees have experienced sufficient warmth, they will become active, bite a hole in the cocoon and emerge into the cell which is formed by the nest wall and the two mud plugs formed by the mother. The males emerge first, typically 4 days to a week in advance of the females. Then the females emerge. The time for the bees to emerge depends on a number of factors, such as the period spent at winter temperatures, the temperature over winter, and the temperature at emergence. In general, the longer the period the bees have spent in winter diapause, the shorter the time required for them to emerge; and the lower the temperature at which the bees have been stored, the longer the time required for them to emerge. FIG. 22 shows typical emergence data derived from incubating four batches of females at different times. It should be stressed that there is great variation in emergence timings.

The effect of cumulative warmth—clearly the stimulus which makes bees emerge in the wild—is the prime stimulus which makes bees emerge. When a bee emerges from winter diapause, it bites through its cocoon as described above, then breaks down the mud plug between its cell and the adjacent cell in the direction of the entrance of the nest. If this cell is still occupied by a dormant bee, the emerged bee ceases to be active and remains in a quasi-dormant state, ie it remains still and waits until the next bee emerges and the way to the entrance to the nest is clear. The emerged bee can now leave the nest. If however the bee blocking the passage does not become active within a day or a few days, the emerged bee will bite at the cocoon to provoke activity in the dormant bee.

The critical point of the process is ensuring that sufficient males and females have emerged to be put into the orchards, fields, etc as the flowers of the target crop open. In order to do this, two parallel phenomena need to be considered. The first is when are the flowers going to open? The grower and the pollinator liaise over this, with predictions being made on personal observation and past experience. The nearer it is to flowering, the more accurate the date of first flowering can be forecast. For example, in the almond industry, the stages of flower development are termed dormant; green tip; pink bud; popcorn; flower; and petal fall, and archive data for the dates of each of these stages for the main tree varieties in various locations in the California Central Valley are available online to growers and others. As the trees pass through these stages, a reasonably accurate impression can be formed as to the date bees will need to be introduced to the orchard for pollination. In a similar way, although less formally and to a lesser degree, data on flowering of other tree crops is available.

Figure 23:
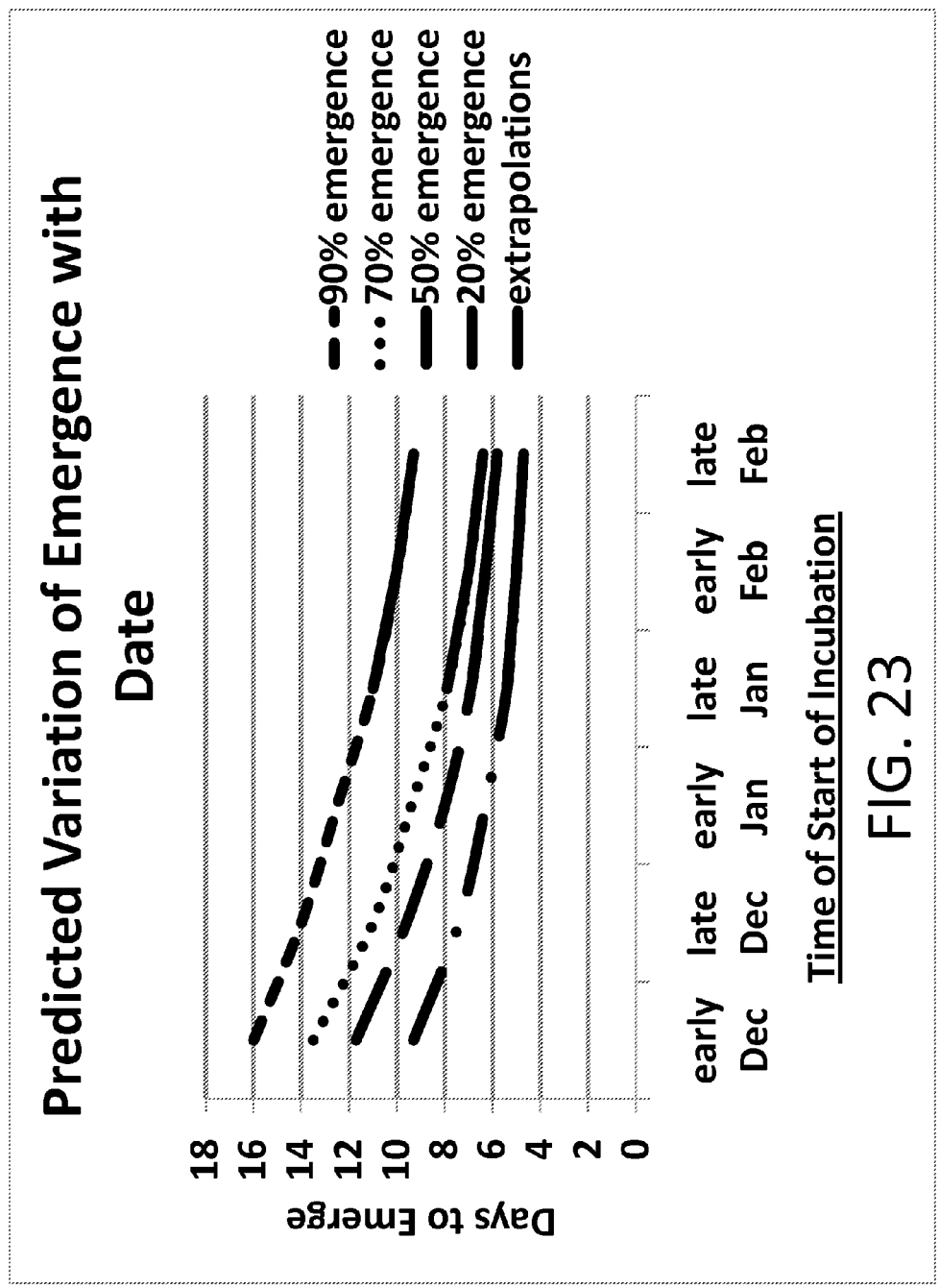
FIG. 23 is an example of a chart which may be prepared to predict how bees will emerge over a particular period of time.

The second factor is how long will it take to warm up the bees to emergence? It has been noted that different populations respond differently. In order to determine the rates of emergence for males and females of a particular population, it is suggested that four test incubations are carried out, preferably ten weeks, eight weeks, six weeks and four weeks before the anticipated date of flowering and the results charted. Typical trial incubation results are shown in FIG. 22. By extracting data points (for example, times to emerge 20%, 50%, 70% and 90% of each batch) from these charts, it is possible to extrapolate from the current data and produce a predictive chart as shown in FIG. 23, which gives accurate data on how bees will emerge on any date up until the end of February say. With a reasonable estimate of when the target trees are likely to flower, the operator can refer to the predictive charts for the bee population to be used, and can read off how many days or hours of incubation will be necessary to get any particular percentage of bees emerged for that date. An optional approach would be to generate predictive charts for different temperatures of incubation, and the timing of emergence controlled by adjusting the incubation temperature.

The operator may therefore develop this type of data and use it to answer management questions, for example, how many cocoons should be at the start of incubation on what date in order to ensure that say 100,000 females are flying by a specific target date?

By the use of statistical methods and fine control, the invention is capable of providing large numbers of bees accurately on precise dates.

Description of Method of Use of the Apparatus which Ensures Emergence Matches Crop Flowering When a small number of bees are available the operator has no option but to handle them all as one batch. For example, it may be that only 100,000 females are available, which may be regarded as sufficient to pollinate one orchard. In this case the bees need to be handled as a batch, and incubation is carried out with the aim of having the bulk of the females emerged and ready to fly on a specific date that the trees are expected to be in say 5% flower. This means that many of the bees will have inevitably emerged several days in advance and will have been chilled well in advance of deployment in the orchard, which may reduce their effectiveness as pollinators.

However, when the operation reaches a certain scale, say for example it has 5 million bees or more, a method of use for the present invention confers a potent advantage which will be illustrated as follows. Instead of processing one batch of bees destined for deployment in one location, the unit can be managed to provide a steady stream of bees emerging in such a way that each day the number of bees required for deployment on that day are available, newly emerged. In that way very few bees have to spend more than a few hours in cold store after emergence. Each bee reaches the point of emergence, walks out of the process chamber 42 into the flight chamber 44 (and optionally flies to the chilling station 212). It is chilled shortly afterwards, held at a cool temperature briefly, packaged, transported in an insulated container, to the orchard where the container is deployed, and allowed to warm up and exit the container. No bee is held at high temperatures for long periods, and no bee is held at low temperatures for long periods. These bees arrive at the orchard in the optimum condition.

Figure 24:
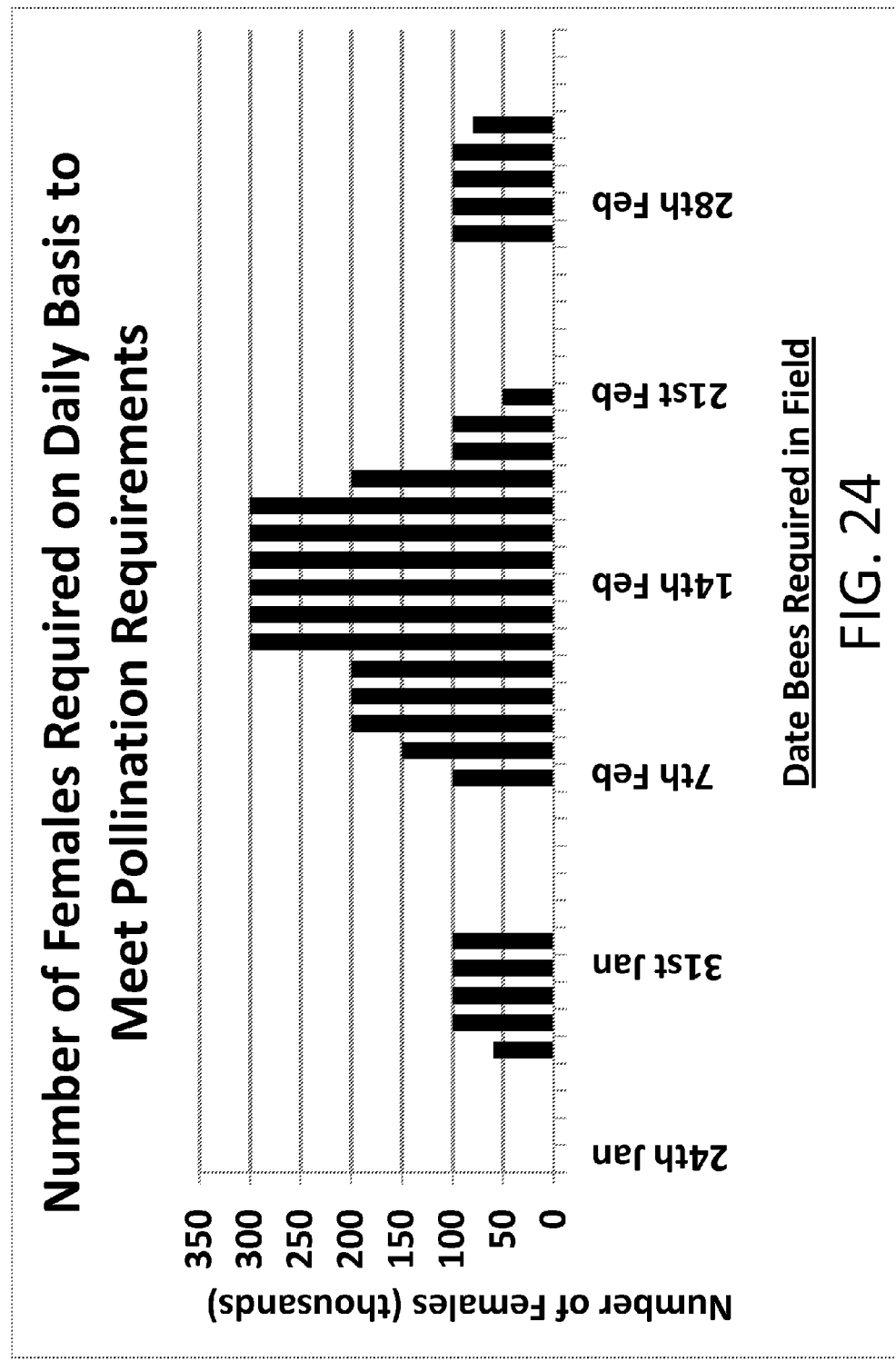
FIG. 24 is a chart showing the relationship between the number of female bees required for a particular period of time.
Figure 25:
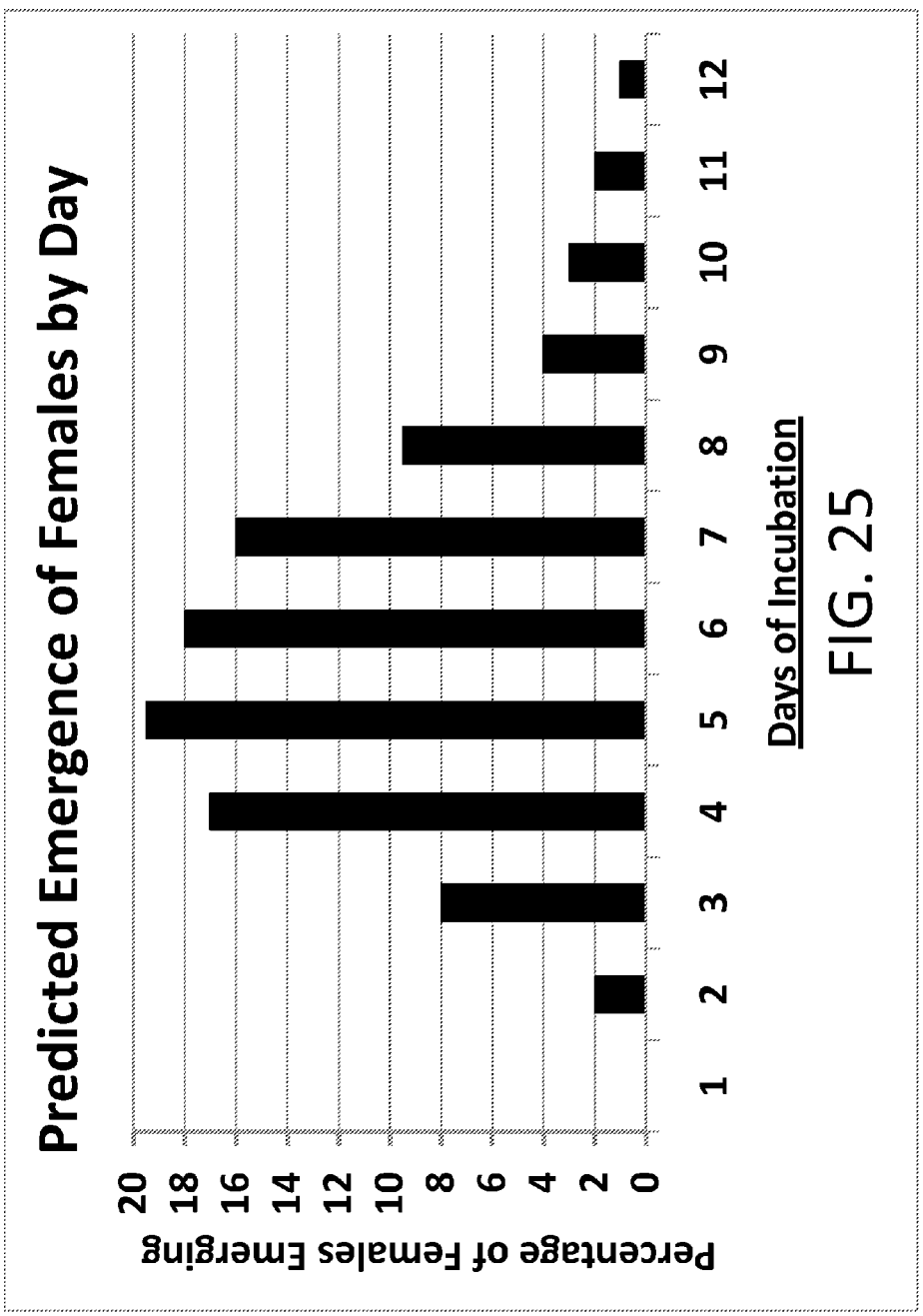
FIG. 25 is a chart showing the predicted emergence of female bees during a cycle of incubation according to the present method.
Figure 26:
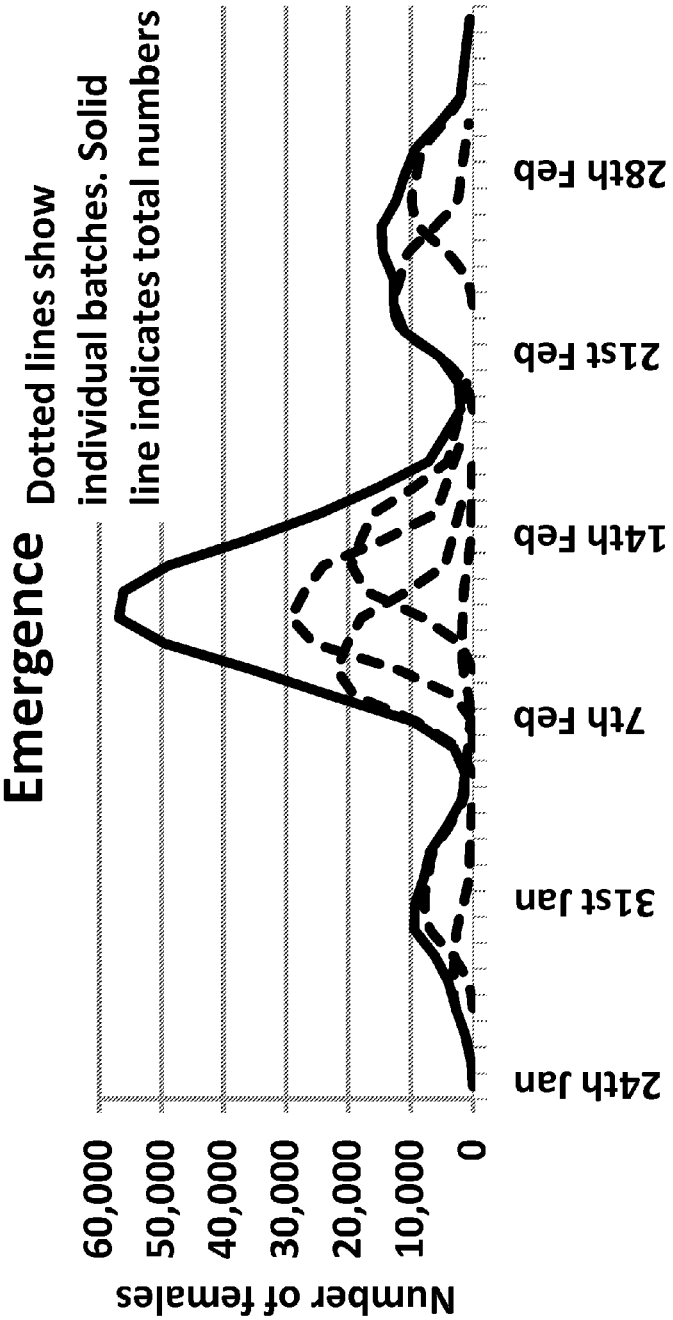
FIG. 26 is a chart showing predicted female bee emergence for multiple incubated batches of bees according to the present method.
Figure 27:
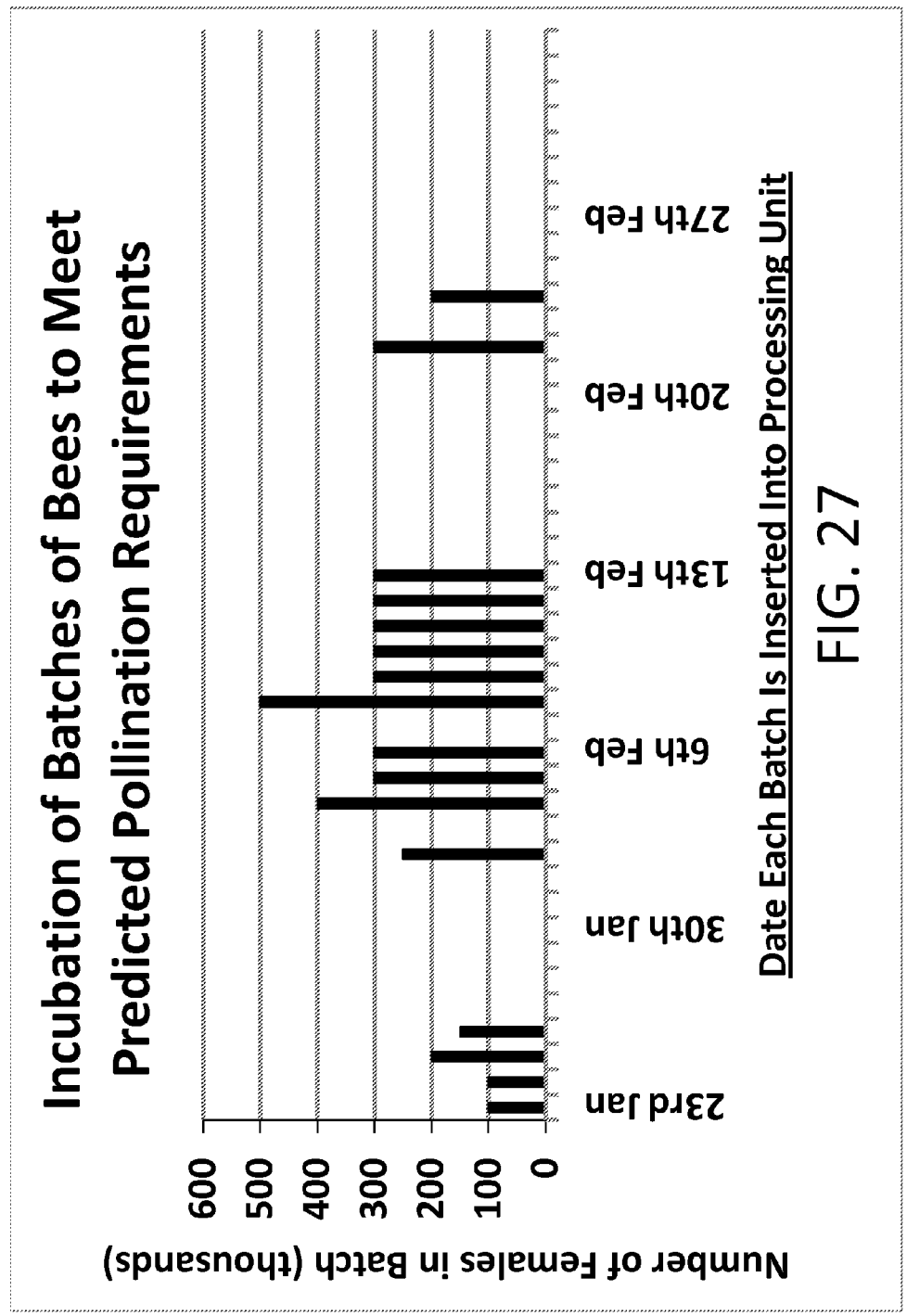
FIG. 27 is a chart showing the incubation of female bees to meet predicted pollination requirements according to the present method.
Figure 28:
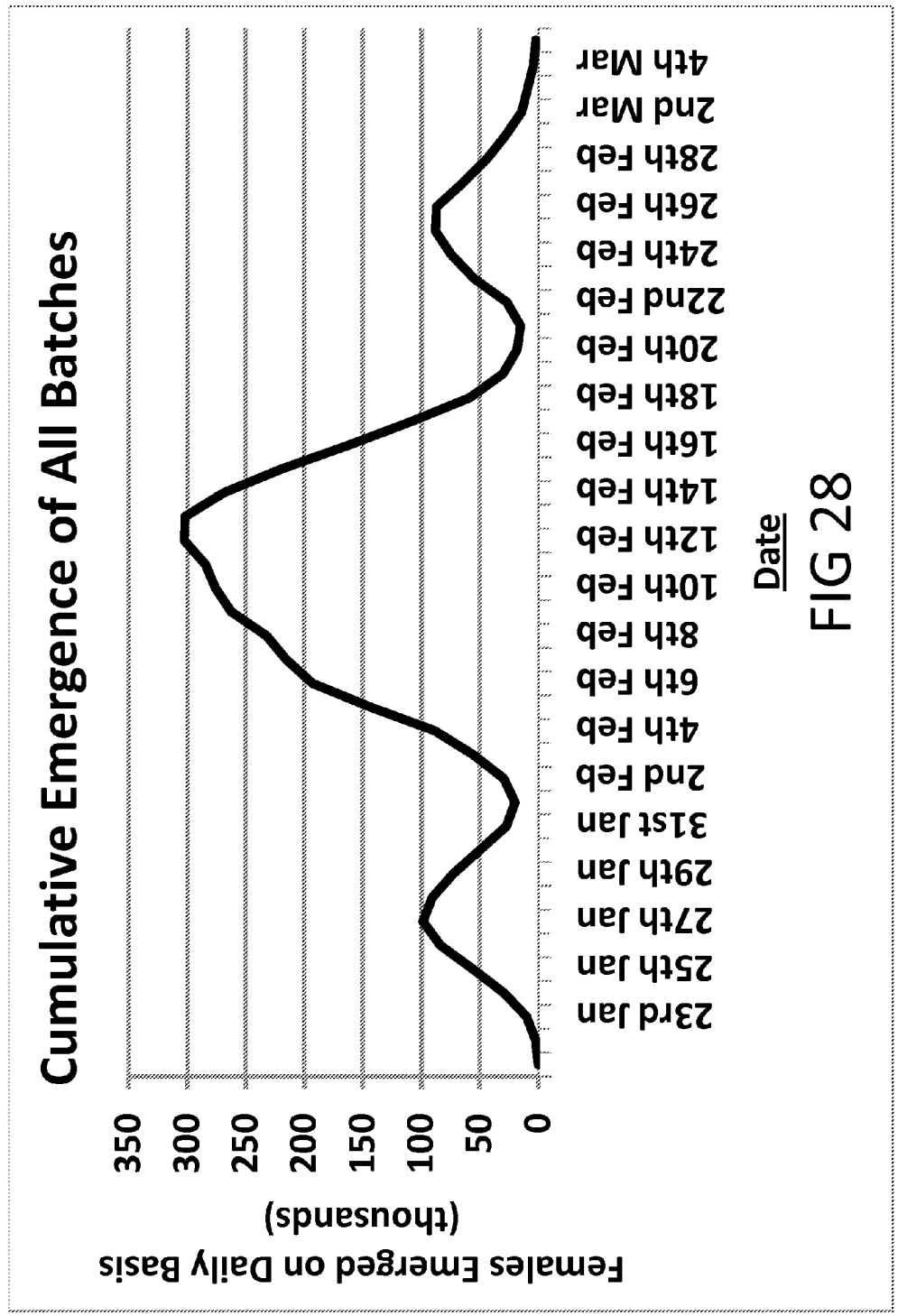
FIG. 28 is a chart showing cumulative emergence of female bees for all batches incubated according to the present method.
Figure 29:
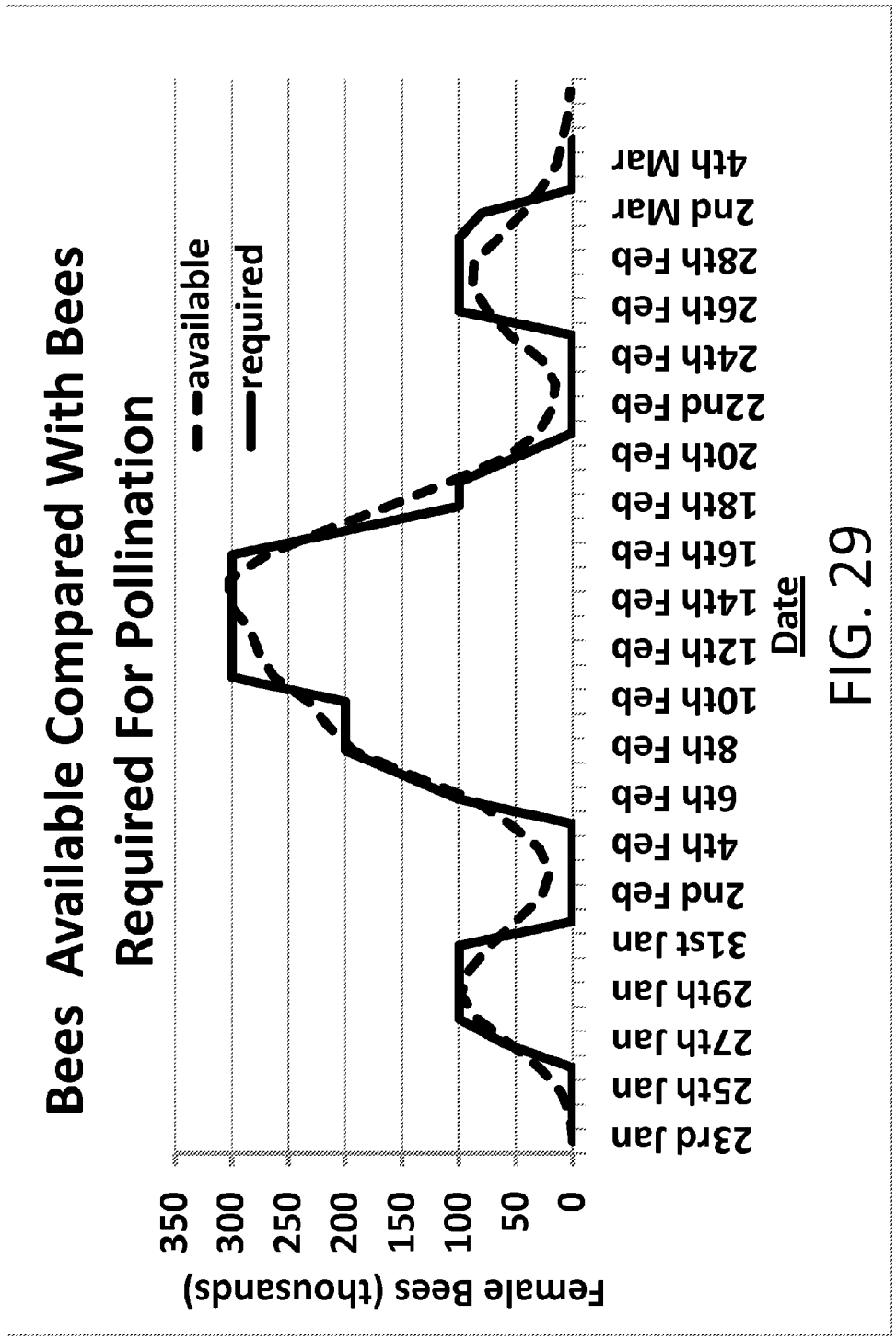
FIG. 29 is a chart showing relationship between the expected female bee emergence according to the present method and the number of bees required for pollination.

To operate embodiments of the apparatus in the continuous process mode, a statistical approach may be followed as illustrated in the charts shown in FIGS. 23-27. As an example, FIG. 23 shows the anticipated demand for bees required for deployment in a number of orchards on the dates as shown. For the purposes of illustration it is assumed that these orchards are in sequence plums, almonds and sweet cherries. FIG. 24 shows the predicted emergence for the bees to be used, which has been extrapolated from test incubations as described previously; females only are shown in this illustration for clarity. This chart shows what percentage of bees will emerge on each day under a given incubation regime. FIG. 25 illustrates how the number of females emerging each day from a number of batches of different size, incubated from different dates, can be found. By a simple iterative process (which may be easily written into a program to give precise results) the manager can determine that by processing 16 batches of bees as shown on FIG. 25, each starting on separate dates as shown, the available bees on each day will be as shown in FIG. 26. When this is compared with the demand, it can be seen that supply can be made to match demand very closely, as shown on FIG. 27. The analysis can be fine-tuned to give a closer match between bees available and bees required. In this way, the operator can produce a stream of bees on a daily basis to meet demand. The current invention will be most efficient and effective when operating in this continuous supply mode, enabling very large numbers of bees to be handled precisely, with minimal handling and labor costs.

While the above is a description of various embodiments of the present invention, further modifications may be employed without departing from the spirit and scope of the present invention. Thus the scope of the invention should not be limited according to these factors, but according to the claims to be filed in the forthcoming utility application.

What is claimed is:

1. A processing unit for solitary bees comprising:
   a) an enclosed process chamber containing a plurality of solitary bees;
   b) an enclosed flight chamber connected to the enclosed process chamber by a plurality of passages, each passage having a height and a length of such size to allow bees to pass through the passage from the process chamber to the flight chamber;
   c) illumination means selectively providing illumination to the flight chamber, the passages being so configured that the illumination to the flight chamber is perceived by bees in the process chamber;
   d) means for providing a periodic flow of chilled air to the flight chamber sufficient to render bees in the flight chamber to an immobile or slow-moving condition; and
   e) collection means for collecting said chilled immobile or slow-moving bees and removing them from the flight chamber.

2. The processing unit of claim 1 further comprising means for providing heated air within the process chamber.

3. The processing unit of claim 1 further comprising means for providing chilled air within the process chamber.

4. The processing unit of claim 1 wherein the illumination means comprises artificial light.

5. The processing unit of claim 1 wherein the illumination means comprises natural daylight.

6. The processing unit of claim 1 wherein the process chamber is enclosed within a larger container selected from the group consisting of a refrigerated shipping container, a structural building, and an industrial air handling unit.

7. The processing unit of claim 1 wherein the process chamber comprises heating, cooling and circulation means providing conditioned air to an inlet plenum connected to the process chamber, an outlet plenum connected to the process chamber, and a return duct for circulating discharged air from the processing unit back to the heating and cooling means.

8. The processing unit of claim 1 wherein means are provided for introducing fresh air to the process chamber.

9. The processing unit of claim 1 wherein the flight chamber comprises a floor and a selectively opened portal and the collection means comprises a collection tray disposed on the floor, the collection tray removable from the flight chamber through the portal.

10. The processing unit of claim 1 wherein the solitary bees in the process chamber are contained within containers selected from the group consisting of loose cocoons, cocoons in straws, cocoons in cardboard tubes, cocoons in sealed nests and cocoons in open tray nests.

11. A processing system for solitary bees comprising:
   a) a plurality of enclosed process chambers, each containing a plurality of solitary bees;
   b) a plurality of enclosed flight chambers, each flight chamber connected to a respective process chamber by a plurality of passages, each passage having a height and a length of such size to allow bees to pass through the passage from the process chamber to the flight chamber;
   c) illumination means for selectively providing either permanent or periodic illumination to any one or more of the flight chambers, the passages being so configured that the permanent or periodic illumination to any one of the flight chamber is perceived by bees in the respective process chambers;
   d) a central plant comprising cooling means for selectively providing a periodic flow of cooled air to any one or more of the flight chambers sufficient to render bees in a selected flight chamber to an immobile condition or slow-moving condition; and
   e) collection means for collecting said chilled immobile bees and removing them from any one of the flight chambers.

12. The processing system of claim 11 wherein the central plant comprises heating means for selectively providing a periodic flow of heated air to any one or more of the process chambers.

13. The processing system of claim 11 wherein the central plant comprises cooling means for selectively providing a periodic flow of cooled air to any one or more of the process chambers.

14. The processing unit of claim 11 wherein the illumination means comprises artificial light.

15. The processing unit of claim 11 wherein the illumination means comprises natural daylight.

16. A method of utilizing solitary bees for the pollination of crops comprising:
   determining the expected flowering dates of the crops;
   calculating the number of solitary bees required for effective pollination of the crops to ascertain a required bee count;
   incubating test groups of solitary bees to ascertain the rate of bee emergence for a given incubation period;
   placing a plurality of bees comprising at least the required bee count within a processing unit, the processing unit comprising incubation means, chilling means, and collection means;
   incubating the plurality of bees to emergence;
   chilling the emerged bees to an immobile or slow-moving condition; and
   collecting the chilled immobile or slow-moving bees and removing said chilled immobile or slow-moving bees from the processing unit; and
   delivering the bees to a location proximate to the crops.

17. The method of claim 16 wherein the processing unit comprises an enclosed process chamber and a flight chamber, the flight chamber connected to the enclosed process chamber by a plurality of passages, each passage having a height and a length of such size to allow bees to pass through the passage from the process chamber to the flight chamber.

18. The method of claim 17 wherein the processing unit comprises means for providing a periodic flow of chilled air to the flight chamber sufficient to render bees in the flight chamber to the immobile or slow-moving condition.

19. The method of claim 18 wherein the flight chamber comprises collection means for collecting the chilled immobile or slow-moving bees and removing them from the flight chamber.

20. The method of claim 17 wherein the processing unit comprises illumination means selectively providing illumination to the flight chamber, the passages being so configured that the illumination to the flight chamber is perceived by bees in the process chamber.

* * * * *